United States Patent
Zhang et al.

(10) Patent No.: US 11,593,512 B2
(45) Date of Patent: Feb. 28, 2023

(54) SYSTEMS AND METHODS FOR CROWDSOURCING, ANALYZING, AND/OR MATCHING PERSONAL DATA

(71) Applicant: Massachusetts Institute of Technology, Cambridge, MA (US)

(72) Inventors: Zhizhuo Zhang, Branford, CT (US); Manolis Kellis, Boston, MA (US); Dianbo Liu, Cambridge, MA (US); Anne Kim, Cambridge, MA (US); Lauren Huang, New York, NY (US); Sandeep Nuckchady, Quatre Bornes (MU)

(73) Assignee: Massachusetts Institute of Technology, Cambridge, MA (US)

( * ) Notice: Subject to any disclaimer, the term of this patent is extended or adjusted under 35 U.S.C. 154(b) by 642 days.

(21) Appl. No.: 16/612,993

(22) PCT Filed: May 11, 2018

(86) PCT No.: PCT/US2018/032303
§ 371 (c)(1),
(2) Date: Nov. 12, 2019

(87) PCT Pub. No.: WO2018/209222
PCT Pub. Date: Nov. 15, 2018

(65) Prior Publication Data
US 2020/0202038 A1    Jun. 25, 2020

Related U.S. Application Data

(60) Provisional application No. 62/632,330, filed on Feb. 19, 2018, provisional application No. 62/505,822, filed on May 12, 2017.

(51) Int. Cl.
*G06F 21/62* (2013.01)
*G16H 10/40* (2018.01)
(Continued)

(52) U.S. Cl.
CPC ...... *G06F 21/6245* (2013.01); *G06F 9/45558* (2013.01); *G06F 16/2365* (2019.01);
(Continued)

(58) Field of Classification Search
CPC ............... G06F 21/6245; G06F 21/602; G06F 16/2365; G06F 9/45558;
(Continued)

(56) References Cited

U.S. PATENT DOCUMENTS 7,461,249 B1 * 12/2008 Pearson ................ G06F 21/57
713/193
8,340,914 B2   12/2012 Gatewood et al.
(Continued)

FOREIGN PATENT DOCUMENTS

EP   2324127 B1   1/2015
EP   2635704 B1   4/2017
(Continued)

OTHER PUBLICATIONS

Nath, Indranil. "Data exchange platform to fight insurance fraud on blockchain." 2016 IEEE 16th international conference on data mining workshops (ICDMW). IEEE Computer Society, 2016 (Year: 2016).*

(Continued)

*Primary Examiner* — Syed A Zaidi
(74) *Attorney, Agent, or Firm* — Wolf, Greenfield & Sacks, P.C.

(57) ABSTRACT

Described herein are a secure system for sharing private data and related systems and methods for incentivizing and validating private data sharing. In some embodiments, private data providers may register to selectively share private data under controlled sharing conditions. The private data may be cryptographically secured using encryption information corresponding to one or more secure execution
(Continued)

environments. To demonstrate to the private data providers that the secure execution environment is secure and trustworthy, attestations demonstrating the security of the secure execution environment may be stored in a distributed ledger (e.g., a public blockchain). Private data users that want access to shared private data may publish applications for operating on the private data to a secure execution environment and publish, in a distributed ledger, an indication that the application is available to receive private data. The distributed ledger may also store sharing conditions under which the private data will be shared.

21 Claims, 24 Drawing Sheets

(51) Int. Cl.
G16H 50/30 (2018.01)
G16H 50/70 (2018.01)
G06F 16/23 (2019.01)
G16B 30/10 (2019.01)
G16B 20/20 (2019.01)
G16B 20/40 (2019.01)
G16B 50/40 (2019.01)
G06F 9/455 (2018.01)
G06F 21/60 (2013.01)
G06Q 50/26 (2012.01)
H04L 9/30 (2006.01)

(52) U.S. Cl.
CPC ......... G06F 21/602 (2013.01); G06Q 50/265 (2013.01); G16B 20/20 (2019.02); G16B 20/40 (2019.02); G16B 30/10 (2019.02); G16B 50/40 (2019.02); G16H 10/40 (2018.01); G16H 50/30 (2018.01); G16H 50/70 (2018.01); H04L 9/30 (2013.01); *G06F 2009/45587* (2013.01)

(58) Field of Classification Search
CPC .......... G06F 2009/45587; G16B 30/10; G16B 20/20; G16B 20/40; G16B 50/40; G06Q 50/265; H04L 9/30
See application file for complete search history.

(56) References Cited

U.S. PATENT DOCUMENTS

| | | | |
|---|---|---|---|
| 9,378,380 B1 * | 6/2016 | Reid | G06F 21/602 |
| 2004/0229231 A1 | 11/2004 | Frudakis et al. | |
| 2010/0113295 A1 | 5/2010 | Norviel | |
| 2011/0105353 A1 | 5/2011 | Lo et al. | |
| 2011/0258326 A1 * | 10/2011 | Hu | H04L 63/062 |
| | | | 726/3 |
| 2013/0085980 A1 | 4/2013 | Alemi | |
| 2013/0096943 A1 * | 4/2013 | Carey | G06F 21/6263 |
| | | | 705/2 |
| 2013/0097644 A1 * | 4/2013 | Brande | H04N 21/8586 |
| | | | 725/93 |
| 2015/0242816 A1 * | 8/2015 | Srimushnam | G06Q 10/107 |
| | | | 705/321 |
| 2015/0310188 A1 * | 10/2015 | Ford | G06F 21/10 |
| | | | 726/28 |
| 2015/0356243 A1 | 12/2015 | Andreassen et al. | |
| 2016/0295384 A1 * | 10/2016 | Shan | H04W 4/08 |
| 2017/0111175 A1 * | 4/2017 | Oberhauser | H04L 63/126 |
| 2018/0165466 A1 * | 6/2018 | Rad | H04N 19/154 |
| 2018/0227275 A1 * | 8/2018 | Russinovich | H04L 9/3236 |
| 2018/0285594 A1 * | 10/2018 | Jarvis, II | G06F 21/6245 |
| 2018/0309567 A1 * | 10/2018 | Wooden | G06F 21/57 |
| 2018/0309747 A1 * | 10/2018 | Sweet | G06F 9/45558 |
| 2020/0145793 A1 * | 5/2020 | Coulbourne | H01L 33/54 |

FOREIGN PATENT DOCUMENTS

| | | |
|---|---|---|
| WO | WO 2014/101126 A1 | 7/2014 |
| WO | WO 2016/063092 A1 | 4/2016 |

OTHER PUBLICATIONS

Xia Q, Sifah EB, Smahi A, Amofa S, Zhang X. BBDS: Blockchain-based data sharing for electronic medical records in cloud environments. Information. Apr. 7, 2017;8(2):44 (Year: 2017).*
NPL Search Terms (Year: 2022).*
International Preliminary Report on Patentability for International Application No. PCT/US2018/032303 dated Nov. 21, 2019.
PCT/US2018/032303, Nov. 21, 2019, International Preliminary Report on Patentability.
[No Author Listed], Demos for AncestryDNA workshop at 2016 CEHG Symposium, Stanford University. GitHub. Mar. 2, 2016:6 pages, https://github.com/snehitp/cehg16-workshop [last accessed May 26, 2020].
[No Author Listed], Ethereum. Ethereum. May 22, 2020:3 pages. https://www.ethereum.org/ [last accessed May 26, 2020].
[No Author Listed], GWAS Catalog. National Human Genome Research Institute. May 17, 2020:3 pages. https://www.ebi.ac.uk/gwas/ [last accessed May 26, 2020].
[No Author Listed], $H^2DB$: Heritability Database Annotating with Trait-Associated Genomic Loci. NIG Genome Informatics Laboratory. 2012:1 pages. http://tga.nig.ac.jp/h2db/ [last accessed May 26, 2020].
[No Author Listed], NVIDIA Research: First Privacy-Preserving Federated Learning System for Medical Imaging. YouTube. Oct. 13, 2019:13 pages https://www.youtube.com/watch?v=Jy7ozgwovgg&feature=youtu.be&ncid=so-elev-78194#cid=nr01_so-elev_en-us [last accessed Apr. 9, 2020].
[No Author Listed], Welcome to Open SNP. Open SNP. 2020:2 pages. https://opensnp.org/ [last accessed May 26, 2020].
Alexander et al., Fast model-based estimation of ancestry in unrelated individuals. Genome research. Sep. 1, 2009;19(9):1655-64.
Auton et al., A global reference for human genetic variation. Nature. Oct. 2015;526(7571):68-87.
Hill et al., Data and theory point to mainly additive genetic variance for complex traits. PLoS genetics. Feb. 2008;4(2):1-10.
Howie et al., Fast and accurate genotype imputation in genome-wide association studies through pre-phasing. Nature genetics. Aug. 2012;44(8):955-960.
Lambert et al., Meta-analysis of 74,046 individuals identifies 11 new susceptibility loci for Alzheimer's disease. Nature genetics. Dec. 2013;45(12):1452-60.
Maes et al., Genetic and environmental factors in relative body weight and human adiposity. Behavior genetics. Jul. 1, 1997;27(4):325-51.
Manichaikul et al., Robust relationship inference in genome-wide association studies. Bioinformatics. Nov. 15, 2010;26(22):2867-73.
McVean et al., An integrated map of genetic variation from 1,092 human genomes. Nature. Nov. 2012;491(7422):56-65.
Ripke et al., Biological insights from 108 schizophrenia-associated genetic loci. Nature. Jul. 2014;511(7510):17 pages.
Rosenbloom et al., The UCSC genome browser database: 2015 update. Nucleic acids research. Jan. 28, 2015;43(D1):D670-81.
Yang et al, Advantages and pitfalls in the application of mixed-model association methods. Nature genetics. Feb. 2014;46(2):100-106.
Zheng et al., LD Hub. Broad Institute. 2016:3 pages. http://.Idse.broadinstitute.org/ [last accessed May 26, 2020].

* cited by examiner

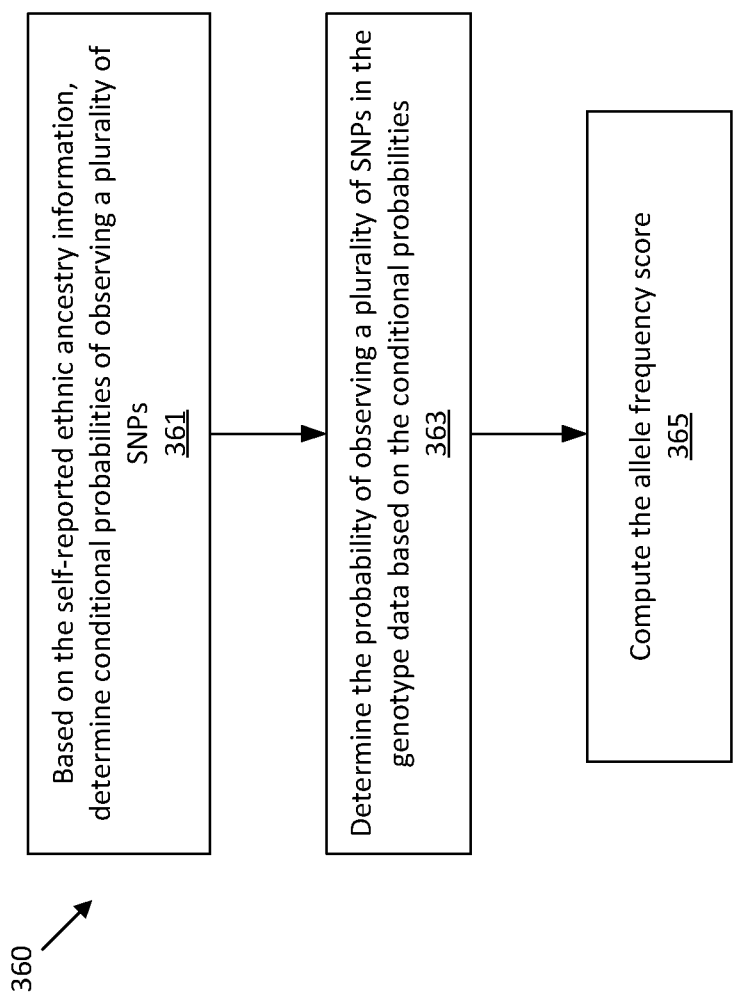

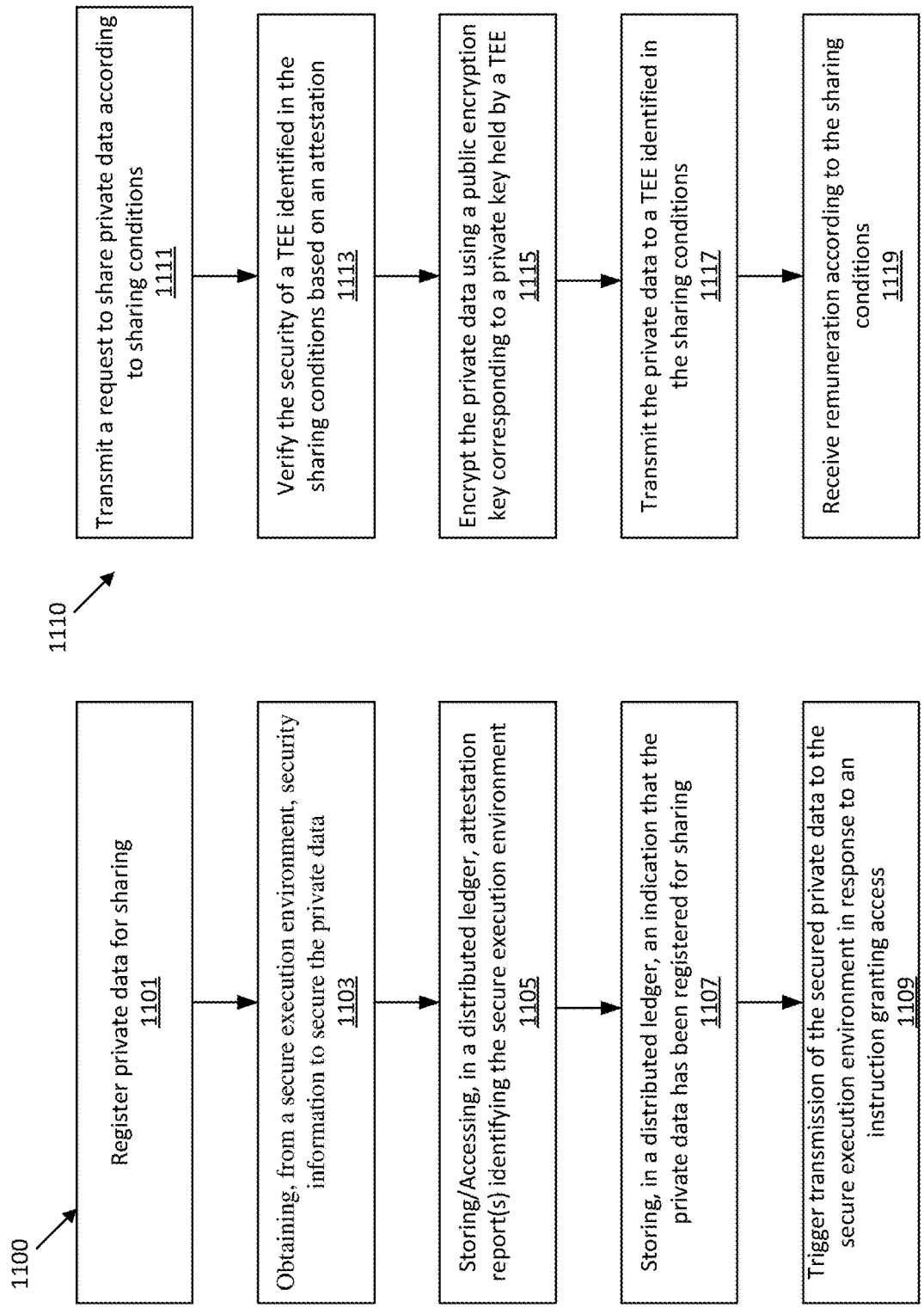

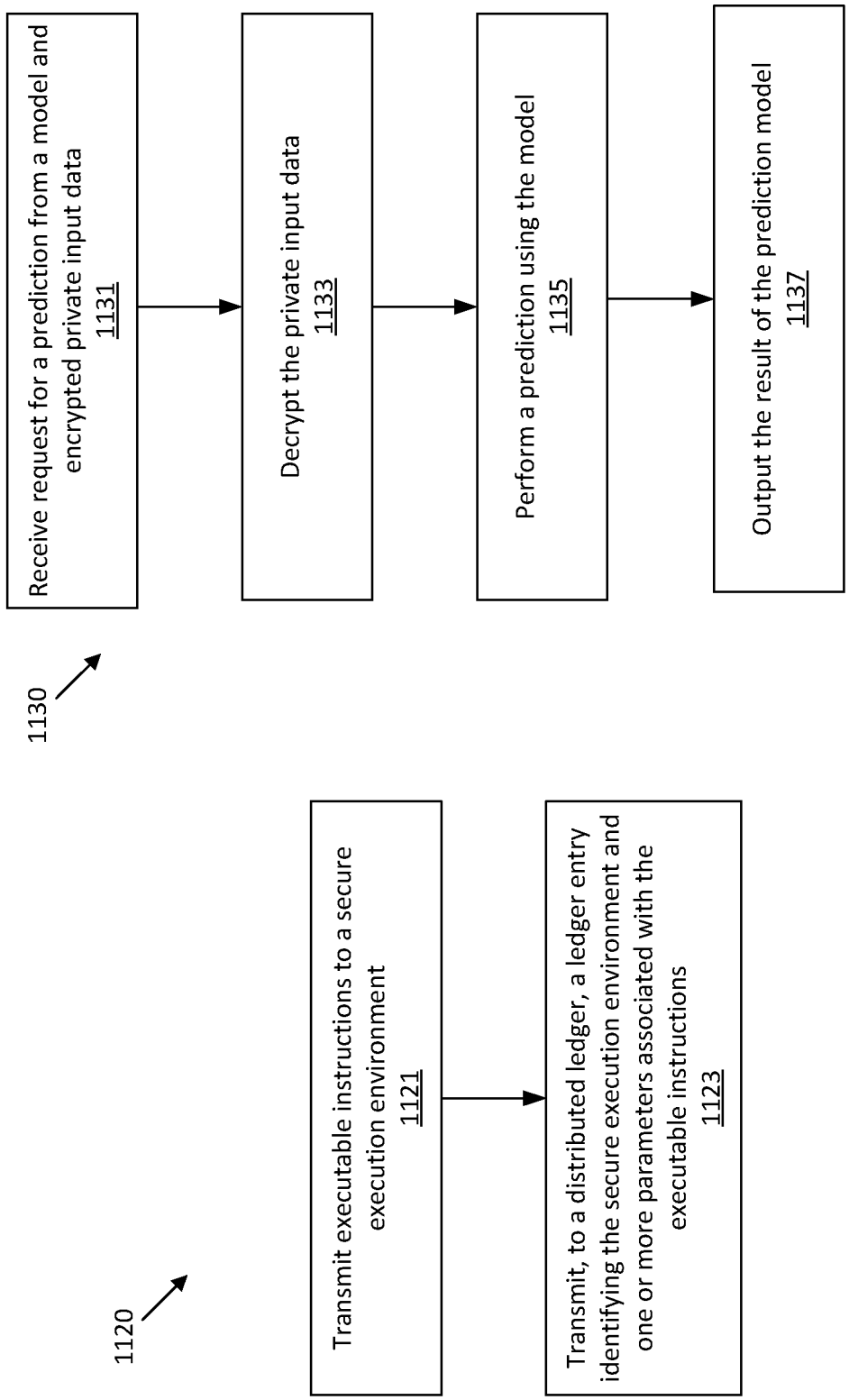

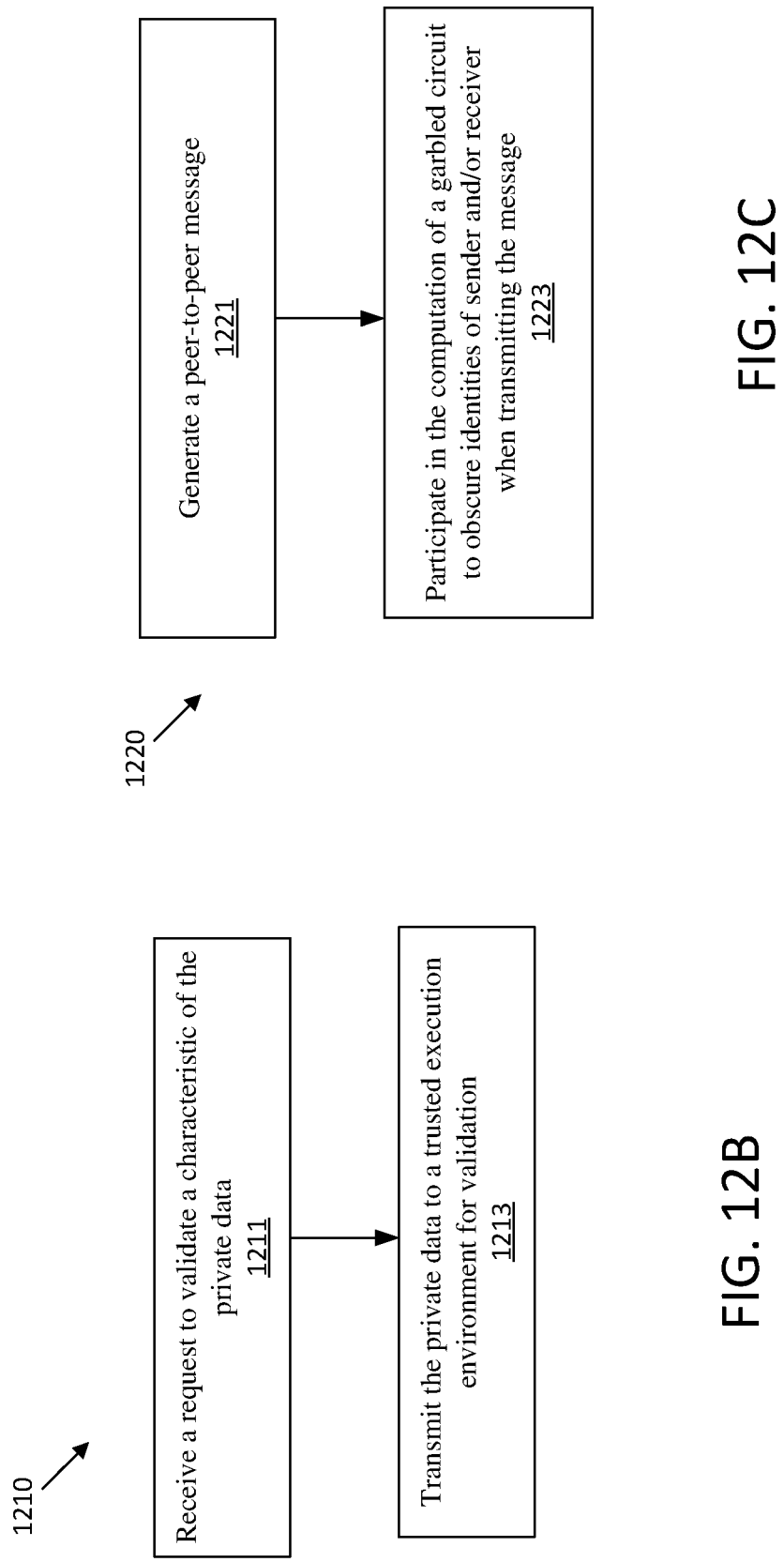

SYSTEMS AND METHODS FOR CROWDSOURCING, ANALYZING, AND/OR MATCHING PERSONAL DATA

CROSS-REFERENCE TO RELATED APPLICATIONS

The present application is a national stage filing under 35. U.S.C. § 371 of international PCT application, PCT/US2018/032303, filed May 11, 2018 and titled "SYSTEMS AND METHODS FOR CROWDSOURCING, ANALYZING, AND/OR MATCHING PERSONAL DATA," which claims priority under 35 U.S.C. § 119(e) to U.S. Provisional Application Ser. No. 62/505,822, filed May 12, 2017 and titled "SYSTEMS AND METHODS FOR CROWDSOURCING, ANALYZING, AND/OR MATCHING PERSONAL DATA" and to U.S. Provisional Application Ser. No. 62/632,330, filed Feb. 19, 2018 and titled "METHODS AND SYSTEMS FOR AN INTEGRATED ARCHITECTURE OF SECURITY HARDWARE AND BLOCKCHAIN FOR A PRIVACY-PROTECTED DATA STORING, PROCESSING AND SHARING MARKETPLACE." The entire contents of these applications are incorporated herein by reference in their entirety.

GOVERNMENT SUPPORT

This invention was made with Government support under Grant Nos. U01 HG007610 and AG054012 awarded by the National Institutes of Health. The Government has certain rights in the invention.

BACKGROUND

A Genome Wide Association Studies (GWAS) may study a genome-wide set of genetic variants do determine associations between single nucleotide polymorphisms (SNPs) and traits. A GWAS may include a significance associated with each SNP that indicates a strength of the association between the respective SNP and the trait.

SUMMARY OF THE DISCLOSURE

Some embodiments provide for secure systems and methods for sharing private data and related systems and methods for incentivizing and validating private data sharing.

In one embodiments, a computer-implemented method for sharing private data is provided. The method includes: registering private data for sharing within a secure platform for exchange of private information, wherein registering the private data comprises: 1) obtaining, from a secure execution environment, security information to secure private data; 2) storing, in the first distributed ledger, an attestation report identifying the secure execution environment has been secured; and 3) storing, in a second distributed ledger, an identification that the private data has been registered for sharing within the secure platform; and in response to receiving an instruction from a user granting access to the secured private data, triggering transmission of the secured private data to the secure execution environment to be processed, wherein the triggering comprises recording in the second distributed ledger an indication that the access has been granted to the secured private data.

In another embodiment, at least one non-transitory computer-readable storage medium having encoded thereon executable instructions is provided. The instructions, when executed by at least one processor, cause the at least one processor to carry out the above method.

In another embodiment, an apparatus is provided. The apparatus includes at least one processor; and at least one storage medium having encoded thereon executable instructions that, when executed by the at least one processor, cause the at least one processor to carry out the above method.

In one embodiment, a computer-implemented method for estimating, based on health information for a population that includes a plurality of people, a likelihood of a first person experiencing a medical condition. The method includes: comparing a first set of nucleotides for condition-associated single nucleotide polymorphisms (SNPs) for the first person to a plurality of sets of nucleotides for condition-associated SNPs, wherein each set of nucleotides for condition-associated SNPs of the first plurality of sets relates to genomic data of a different person of the population; and in response to determining that the first set of nucleotides for condition-associated SNPs exceeds a threshold level of similarity to one or more second sets of nucleotides for condition-associated SNPs of the first plurality, the one or more second sets being respectively associated with one or more people of the population, computing the likelihood that the first person will experience the medical condition based on whether the one or more people of the population have been diagnosed with the medical condition.

In another embodiment, at least one non-transitory computer-readable storage medium having encoded thereon executable instructions is provided. The instructions, when executed by at least one processor, cause the at least one processor to carry out the above method.

In another embodiment, an apparatus is provided. The apparatus includes at least one processor; and at least one storage medium having encoded thereon executable instructions that, when executed by the at least one processor, cause the at least one processor to carry out the above method.

In another embodiment, a computer-implemented method is provided. The method includes: determining whether genomic data that is alleged to be associated with a person is authentic, wherein the determining comprises: accessing one or more characteristic associated with the genomic data, wherein the accessing comprises: 1) receiving non-genomic information indicating at least one of the one or more characteristics that the person is alleged to possess; and/or 2) computing at least one of the one or more characteristics of the genomic data; comparing the one or more characteristic of the person to the genomic data; and determining a likelihood that the genomic data is authentic based at least in part on a result of the comparing.

In another embodiment, at least one non-transitory computer-readable storage medium having encoded thereon executable instructions is provided. The instructions, when executed by at least one processor, cause the at least one processor to carry out the above method.

In another embodiment, an apparatus is provided. The apparatus includes at least one processor; and at least one storage medium having encoded thereon executable instructions that, when executed by the at least one processor, cause the at least one processor to carry out the above method.

BRIEF DESCRIPTION OF THE DRAWINGS

The accompanying drawings are not intended to be drawn to scale. For purposes of clarity, not every component may be labeled in every drawing. In the drawings:

FIGS. 3A-G show illustrative processes for determining whether genomic data is authentic.

FIGS. 11A-D show illustrative process flows for sharing private data.

FIGS. 12A-C show illustrative process flows for search and communication regarding private data.

DETAILED DESCRIPTION

Figure 1:
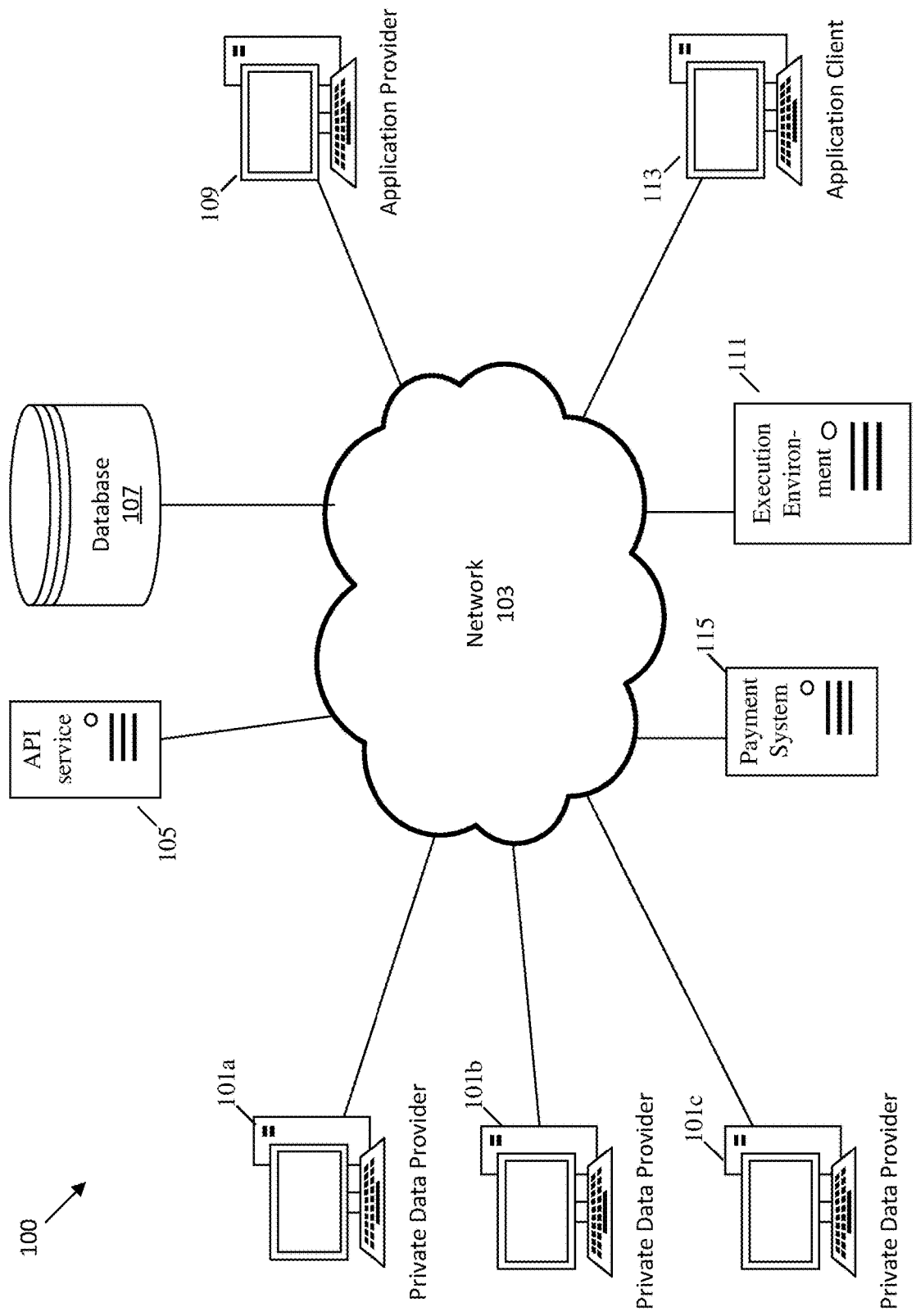
FIG. 1 shows an illustrative system for sharing private data in which some embodiments of the technology described herein may operate.

Described herein are a secure system for sharing private data and related systems and methods for incentivizing and validating private data sharing. In some embodiments, private data providers may register to selectively share private data under controlled sharing conditions. The private data may be cryptographically secured using encryption information corresponding to one or more secure execution environments. To demonstrate to the private data providers that the secure execution environment is secure and trustworthy, attestations demonstrating the security of the secure execution environment may be stored in a distributed ledger (e.g., a public blockchain). Private data users that want access to shared private data may publish applications for operating on the private data to a secure execution environment and publish, in a distributed ledger, an indication that the application is available to receive private data. The distributed ledger may also store sharing conditions under which the private data will be shared. Once a private data provider grants access to private data, for example by agreeing to the sharing conditions, the private data may be transmitted to and operated on by the application in the secure execution environment.

Also described herein are methods for detecting potentially inauthentic private data. In some embodiments, private data users are interested in performing research tasks on genomic data and may benefit from having an indication of the likelihood that the genomic data is inauthentic. When private data is potentially or likely inauthentic (e.g., the likelihood that it is inauthentic is above a threshold), a data user may choose not to use the private data or may use the private data in a manner different from private data that is likely authentic. In some embodiments, the genomic data alleged to be for an individual is received (e.g., by an application in a secure execution environment) with reported characteristics (e.g., biological sex, ethnic ancestry, and/or phenotypical traits) that are allegedly possessed by the alleged individual to which the genomic data relates. It may be determined how likely one or more of the characteristics are to correspond to the genomic data in order to determine how likely the genomic data is to be authentic. In some embodiments, one or more characteristics may be computed from the genomic data instead of or in addition to the received characteristics. The computed characteristics may be used to determine the likelihood that the genomic data is authentic or is inauthentic (e.g., is randomly generated data, or is engineered genomic data rather than natural genomic data).

Also described herein are methods for estimating a likelihood that a person will experience a medical condition, which in some cases may be estimated by an application in a secure execution environment. Based on private data including genomic data and medical condition statuses shared by a population, the genomic data of an individual may be matched to a subset of the population with sufficiently similar genomic information. The medical condition statuses of the subset of the population may then be used to determine the likelihood that the individual will experience the medical condition.

The inventors have recognized and appreciated that it may be desirable to allow for the secure sharing of private data. For example, many research tasks, such as those that include generation of models describing a population (e.g., of people, or of another subject) and that may be used to make predictions about the population or members of the population, may benefit from the sharing of large amounts of data. In many of these cases, the data that is sought may be sensitive to a person who generates the data or to whom the data pertains, or that data may be or remain valuable or more valuable only as long as it remains private and is otherwise not publicly distributed and is not copied. Such private data may include, but is not limited to, social information data, social media data, accounting data, inventory data, consumer data, image data, medical records, financial data, insurance data, genomic data, and/or phenotypic data. (For ease of description below, some embodiments are described with reference to the data being private genetic data that may include genomic/genotypic and phenotypic data. It should be appreciated that the private genetic data is used as an illustrative example that is not meant to be limiting, and that some embodiments are not limited to operating with a particular type of private data.) Some embodiments described herein may include techniques that may be applied to the secure sharing of any private data, so as to provide confidentiality and security when private data is to be exchanged. In addition, some embodiments described herein may include techniques for incentivizing and/or remunerating data providers, to further encourage sharing of data that is conventionally kept private but that may be beneficial when contributed to a research task.

For example, such techniques may be used with genetic data. Medical researchers have recognized that many complex diseases like Alzheimer's disease and Schizophrenia have a significant genetic contribution. For instance, there may be more than tens of deoxyribonucleic acid (DNA) single-nucleotide polymorphisms (SNPs) involved in a disease process. Some conventional modeling approaches for medical conditions attempt to build a universal mathematical model to map a DNA sequence to a disease status. For example, a linear mixed-effects model may be built to predict disease risk given genotype data. The inventors have recognized and appreciated, however, that such a mathematical modeling approach for predicting disease risk may not be effective because of insufficiency of data. For instance, currently-available genetic and disease status data may not include enough samples to allow construction of a mathematical model to capture complex genetic architectures (e.g., interactions between different genes).

For instance, if one can robustly estimate the parameters for a model without SNP interaction information using at least n samples, then to robustly estimate all the parameters for the a model including SNP interaction information, order of $n^2$ samples may be needed, which is much larger. Currently, GWAS may be conducted using about 10,000 to 100,000 samples, which may not be sufficient for construction of a model with SNP interaction.

Additionally, conventional parametric modeling may not take into account contributions of rare variants. The inventors have recognized and appreciated that, in building a parametric model, allele frequencies may have an impact on parameter values calculated by a parameter estimation process. Yet it is common practice to filter out variants that are relatively rare (e.g., allele frequency <5%) before fitting the parametric model. As a result, contribution from such variants may be lost. On the other hand, monozygotic twins share 100% identical DNA, and many studies on twins have shown higher concordance rates between monozygotic twins for many complexity diseases such as Alzheimer's disease. Thus, disease status for one twin sibling may be reliably predicted using health information of the other twin sibling, without building any universal parametric model.

More and more people are obtaining their DNA genotype data, and different companies provide services to add value on the DNA data and encourage people to upload their own DNA data. The most common form of DNA data is SNP data, which only contains the genotype of common SNPs in the genome. (As used herein, SNP may refer to a particular base position within a genome, and nucleotide may refer to the status of a particular SNP.) For example, companies such as 23andme and ancestry.com provide genotype information for 600,000 SNPs.

The inventors have recognized that it may be beneficial in some contexts, and may improve modeling for research projects, to collect large amounts of private data from individuals. Other contexts include aggregating data from distributed private data sources, which while challenging, takes many forms such as medical data, financial data, social media data and others forms. Examples of these data sources include, but are not limited to, GWAS, electronic medical records, medical images, phenotypes, research results, credit scores, consumer and equity transactions, accounting and inventory data, social media and internet history, processing conditions in manufacturing, and personal preferences.

For example, modeling for medical research may be improved if the private genomic or research data, that is available now to select organizations or individuals could be made securely available to more medical researchers in need of data for new medical discoveries.

As another example, modeling business processes may be improved if the private upstream supplier data or downstream consumer data, that are held by individuals, could be made securely available to businesses in need of data for better business planning.

As a further example, modeling social media behavior may be improved if the private social media and Internet data available now to select platform organizations, could be made securely available to advertising and consumer product companies, governments and political parties, and other platforms seeking personal data to improve their products and operations.

Larger volumes of private data sharing, and modeling based on that data, may raise two concerns relating to the sources of such private data.

First, the people to whom the private data relates may have concerns regarding who may access their private data and for what purpose the private data will be used, and may have concerns regarding whether the private data will be handled and stored in a secure manner to prevent improper or unauthorized access. Techniques described herein for secure exchange and sharing of private data may mitigate this first concern in some circumstances, as described in detail below.

Second, the inventors recognized and appreciated that if individuals are being asked to contribute private data on a wide scale, the likelihood of individuals contributing such private data may increase if the individuals are incentivized or remunerated in some manner. However, conventional methods of remuneration may not be desirable for data sharing. For example, fiat currency transfers may require trust between parties and/or the sharing of financial information that parties may prefer to have remain private. Furthermore, agreeing to any schedule of payments may require significant trust. For example, in some applications, it may be desirable to share data in exchange for payments rendered upon use of the data. Individuals sharing the data may have little or no visibility into actual uses of the data and whether payment is being rendered accurately. Additionally, some data may be shared once, for example to train a model, and a trustworthy method of negotiating the value of a particular contribution and remunerating data providers may not be possible with conventional means. Moreover, incentives to share data may also incentivize the sharing of fraudulent data. For example an individual may obtain and share inauthentic DNA data in multiple ways, for example by 1. copying another person's DNA data; 2. randomly generating genotype data; 3. obtaining non-human DNA data. Especially in situations where the genetic data is self-reported by anonymous contributors, it may be beneficial to detect inauthentic DNA in order to ensure that the shared data is valuable.

The inventors have thus recognized and appreciated the desirability of techniques that can incentive private data sharing, while also detecting and preventing distribution of fraudulent data, and/or flagging suspicious data such that those to whom the suspicious private data is distributed may be alerted to the potential for the data to be fraudulent and may interact with the data as appropriate.

Accordingly, some embodiments include a secure platform for allowing individuals to share data. In some embodiments, individuals may register for sharing private data (e.g., genetic data including nucleotide data at a plurality of SNPs). In some embodiments, data providers may register, for example using a registration application programming interface (API) implemented by a server, to receive sharing credentials such as a user identification and cryptographic information, such as public and private cryptographic keys, that may be used to access secure systems for data sharing.

In some embodiments, data providers may register for sharing data in one or more distributed ledgers. A distributed ledger, such as a blockchain, may be shared among multiple nodes in a network and used to record and check transactions in a cryptographically-secure manner. For instance, in some embodiments, while new transactions may be appended to the distributed ledger, past transactions may not be altered without breaking a chain of cryptographic proofs. Thus an entry accepted into the distributed ledger may be immutable and trusted. A distributed ledger may therefore be used in applications other than digital currency. For instance, a distributed ledger may be used to implement a trust structure to allow attestations (e.g., computer security attestations) to be relied upon across multiple entities. In some embodiments, a distributed ledger may be used to record attestations by trusted entities, so that other entities need not independently verify the attested facts.

In some embodiments, the data providers may register to share data by interacting with a distributed ledger, for example by submitting a request to nodes maintaining the distributed ledger to execute instructions stored in the distributed ledger (e.g. a smart contract) and/or record that the user is providing data in the distributed ledger. In some embodiments, private data providers and users, such as individuals using the data to train models or purchasing access to models, may interact with the distributed ledger using a distributed application client.

In some embodiments, the private data may be secured via a secure, trusted execution environment (TEE), which may be a cryptographically secure remote computing device. For example, Intel Corporation® Software Guard Extensions (Intel® SGX) or ARM® TrustZone may be used to provide a TEE that allows for data to be operated on securely within the TEE without granting visibility to the data outside the execution environment. In some embodiments, the TEE may only run audited instructions and/or secure virtual machines that limit operations to ensure security. In order to ensure privacy, individuals sharing data may receive a cryptographic key for encrypting data to be sent to the TEE, and, in some embodiments, the private data is only unencrypted within the TEE. For example, an individual who registers to share data may receive a public encryption key that corresponds to a private encryption key secured in the TEE. In order to ensure that the TEE may be trusted, attestations that validate the identity and/or security of the TEE may be published to a distributed ledger. For example, the TEE may be audited in any suitable manner. The attestations may include any suitable identifier of the TEE and/or proofs of security. Once an individual establishes a trusted relationship with the TEE using an attestation, the private data may be secured by encrypting the private data using the encryption key for the TEE. In some embodiments, an indication that the private data has been secured may be stored in the distributed ledger.

In some embodiments, a distributed ledger may be used to store an indication that the private data has been registered for sharing within the secure platform. In such embodiments, a smart contract may be stored in a distributed ledger, for example to control access to the data. The distributed ledger used to store the indication that the private data has been registered for sharing may be the same as or different from any distributed ledger(s) used to register to for sharing private data and/or attest for the security of TEEs. In some embodiments, multiple separate entries may be made in a single distributed ledger. In such embodiments, entries, such as smart contracts, in the distributed ledger may be used to keep different types of ledger entries separated.

In some embodiments, a private data user who wants to use private data, from private data providers, in an application, for example a genomic model for predicting disease risk, may submit computer instructions (e.g., an executable program and/or virtual machine instructions) for executing the application to a TEE. In some embodiments, one or more TEEs may execute one or more virtual machines for executing application, and the virtual machines may allow for a limited set of instructions to ensure security of the private data. The private data user may use the distributed ledger to indicate that the application is available for receiving private data. In some embodiments, the distributed ledger entry may indicate one or more network addresses of the TEE and/or virtual machine executing the application, one or more cryptographic keys or proofs to be utilized to submit private data to the application, or any other suitable information for providing secure submission of private data to the application. In further embodiments, for one or more applications, the private data user may submit one or more smart contracts to the distributed ledger. These smart contracts may specify conditions for sharing of private data. For example the conditions for sharing private data may include a method of determining the value of the private data submitted, a method of remunerating private data contributors, and other conditions.

In some embodiments, private data that was secured using a TEE cryptographic key may be transmitted to a TEE to be decrypted and processed (e.g., for use in training an application) in response to an instruction from a private data provider granting access to the secured private data. For example, the private data provider may use a distributed application client to interact with a smart contract for providing data to an application. This interaction may post an entry to the distributed ledger that access to the private data was granted and, in so doing, bind the private data provider and any private data user to sharing conditions previously published in the distributed ledger.

In some embodiments, private data providers may be remunerated for their contributions using the distributed ledger. It should be appreciated that some distributed ledger implementations, such as the Ethereum network, may be used to publish smart contracts as well as 0 (also referred to as digital currency), which may be used as payment. In some embodiments, private data users may create application tokens (e.g., Ethereum Request for Comment 20 (ERC20) compliant tokens) that are associated with one or more applications and provided in exchange for private data. These application tokens may be used to distribute payment received for access to applications, for example by distributing received payments for access according to the number of tokens held by each private data provider. In some embodiments, payments for access to an application may be directly divided among all or a portion of private data providers, for example as may be governed by a smart contract.

Also described herein is a method for detecting inauthentic private data. The inventors have appreciated that the remunerations that incentivize private data providers to contribute private data may incentivize bad actors to submit fraudulent private data. In some embodiments, it may be beneficial to detect potentially-fraudulent private data. In some embodiments, where the private data is genomic data, non-genomic information may be received along with the genomic data. The non-genomic information may indicate one or more characteristics that are allegedly possessed by a person that is the alleged source of the DNA. For example, the received characteristics may include, but are not limited to, characteristics such as ethnic ancestry, biological sex, and/or phenotypical traits (e.g. hair color, eye color, cleft chin). The one or more characteristics may be compared to the genomic data in order to determine a likelihood that the genomic data is authentic. In some embodiments, traits may be inferred from the genetic information and compared to the received traits. For example, an ethnic ancestry may be inferred from SNPs in the genomic information and compared to the received ethnic ancestry. As another example, the heterozygosity of sex chromosome SNPs may be used to determine if the received biological sex corresponds to the genomic data. In some embodiments, one or more characteristics may be determined based on the genomic data instead of or in addition to the received characteristics. For example, certain SNPs tend to exhibit natural levels of correlation in authentic genomic data. A computed measure of correlation between these SNPs in the received data may be used to compute a likelihood that the DNA is authentic. In some embodiments, multiple characteristics may be used to determine multiple likelihoods that the genomic data is authentic; these likelihoods may be combined in order to determine an overall likelihood that the genomic data is authentic. The genomic data may be determined to be authentic if the likelihood of authenticity exceeds a threshold.

Also described herein is a method for estimating, based on private data including health information for a population, a likelihood of a first person will experience a medical condition. The inventors have appreciated that high concordance rates of medical condition status (e.g., whether a diagnosis of presence of a particular medical condition, such as a disease, has been made) between twin siblings may occur because twin siblings share a same set of condition-risk variants in their genome. Thus, there may be high concordance rates of medical condition status between two people who share a same set of condition-risk variants in their genome, even if these people are not twin siblings. Accordingly, in some embodiments, a computational approach is provided for identifying pairs of individuals from the population of private genomic data who share a same set of condition-risk variants for a given complex disease. Such pairs may be referred to as "pseudo twins."

A pseudo-twin model may be configured, for example in a TEE, to receive private genomic data, and corresponding disease diagnoses and/or statuses, from a population of individuals. The pseudo-twin model may filter the genomic data to identify condition-associated SNPs for a particular medical condition. Filtering may include, but is not limited to, identifying SNPs with genome wide association study (GWAS) p-values that exceed a threshold and removing SNPs that are highly correlated with one or more other SNPs with sufficiently high p-values. These SNPs may then be used to determine one or more pseudo-twin model parameters.

The pseudo-twin model may then be applied to estimate a risk of a medical condition for an individual. The pseudo-twin model receives genomic data from the individual and compares condition-associated SNPs in the received genomic data to the population data. When the received genomic data exceeds a threshold level of similarity to genomic data in the model, a pseudo-twin is detected. The detected pseudo-twins are then used to determine the likelihood that the individual will experience the medical condition based on whether the one or more pseudo-twins have been diagnosed with the medical condition. For example, the proportion of pseudo-twins with the disease may be output as the likelihood of experiencing the disease.

Various embodiments are described below, to illustrate how techniques described herein may be implemented. It should be appreciated, however, that the described embodiments are merely examples and that other embodiments are possible.

Further, as discussed above, for ease of description below, some embodiments are described with reference to the data being private genetic data that may include genomic/genotypic and phenotypic data. It should be appreciated, however, that the private genetic data is used as an illustrative example that is not meant to be limiting, and that embodiments are not limited to operating with a particular type of private data.

FIG. 1 provides a description of a computer system with which some embodiments may operate, to provide context for a subsequent description in connection with other figures, of particular techniques that may be used in various embodiments in a system like the one shown in FIG. 1, or other computer systems. Such techniques are described in detail below, following the discussion of FIG. 1.

In particular, FIG. 1 illustrates a system 100 for sharing private data in which some embodiments of the technology described herein may operate. FIG. 1 illustrates private data providers 101a, 101b, and 101c, network 103, API service 105, data store(s) 107, private data users application provider 109 and application client 113, execution environment 111, and payment system 115. The network 103 connects the computing devices, and the system 100 may be operable to securely share private data from the private data providers 101a-101c with private data users, such as the application provider 109 and the application client 113.

Private data providers 101a-101c may be individuals (e.g., humans) and/or organizations (research organizations, such as hospitals, or owners or operators of sets of private data (e.g., an operator of a data store of genomic information for a group of individuals), or other organizations that may be commercial, not-for-profit, and/or non-profit) with any suitable private data for sharing. The private data may be genomic, financial, and/or health data, or other data. The private data providers 101a-101c may use any suitable processing circuitry and/or computing device, such as a desktop or mobile computer, to connect to the network 103 and remote computing devices.

In some embodiments, the private data may be genomic data for an individual and the private data providers 101a-101c may be individuals who obtained their own DNA genotype data. For example, each provider 101a-101c may have provided a DNA sample to a company that sequences the DNA. A common form of DNA data is SNP data, which contains a genotype (e.g., a nucleotide value) of common SNPs (i.e., particular base positions) in the genome. For example, companies such as 23andme and ancestry.com provide consumers with genotype information for 600,000 SNPs. The providers 101a-101c may operate computing devices to interact with other components of the system 100 regarding the private data, via a network 103.

The network 103 may be any suitable wired or wireless network for connecting the private data providers 101a-101c to the private data users and the remote computing devices in the system 100. For example, the network 103 may be a local and/or wide area network including the internet (e.g., a virtual private network, overlay network, and/or internet traffic flows) with connections implemented via 802.11 Wi-Fi, Ethernet, fiber-optics, or any suitable connection. In some embodiments, the network 103 may include an overlay network and/or routing protocol associated with peer-to-peer messaging and/or one or more distributed ledgers. In some embodiments, the network 103 may be an ad-hoc network using any suitable connection. In further embodiments, the network 103 may be or include a wired or wireless local network. In some embodiments, the local network may include wired connections, including Universal Serial Bus (USB), Inter-Integrated Circuit (I2C), Serial Peripheral Interface (SPI), network-on-chip (NOC), Peripheral Component Interconnect Express (PCIe), or any other suitable connection. It should be appreciated, and the inventors have recognized, that various topologies of the network 103 may be better suited for various authentication methods that may be practiced according to the present disclosure.

In the example of FIG. 1, private data providers 101a-101c may use one or more APIs implemented by the API service 105 to interact with other components of the system 100 and control access to and remuneration for contributed private data. The API service 105 may be implemented using any suitable computing device, such as one or more servers.

In other embodiments, the API service 105 may be a distributed ledger. The inventors have recognized that implementing the API service 105 as a distributed ledger may provide substantial benefits/improvements over a single server, since a distributed ledger may provide transparent and trustworthy APIs, for example using one or more smart contracts. Furthermore, distributed ledgers offer high levels of uptime, availability, and overall accessibility. Additionally, implementing the API service 105 allows for flexibility in accepting APIs, such as smart contracts, from private data providers 101a-101c and private data users. Thus, a distributed ledger may improve upon server implemented APIs by allowing for the acceptance and use of user submitted APIs that may be public and immutable and therefore audited and trusted.

In some embodiments, the private data providers 101a-101c may execute, on client devices, a client application that they use to interact with the API service 105. For example, the API service 105 and the computing devices of each of private data providers 101a-101c may implement respective portions of a distributed application. For example, the devices of the private data providers 101a-101c may implement a distributed application client as is described with reference to FIG. 9.

In some embodiments, the private data providers 101a-101c may, via the distributed application, register to share private data using a registration API implemented by the API service 105. The private data providers 101a-101c may receive (via the application) sharing credentials in response to registering. Such sharing credentials may include, but are not limited to, a user identification and cryptographic information.

The user identification may be a unique identification that identifies each private data provider 101a-101c within the system 100. In some embodiments, the private data provider 101a-101c may provide that uniquely identifying credential to the API service 105 as part of registration, and the unique identifier may be used by the system 100 to identify the provider following its receipt. In other embodiments, a user identifier may be a cryptographic key or an identifier based on a cryptographic key. For example, in some embodiments private data providers 101a-101c may be identified within the system 100 by an address used in a distributed ledger protocol such as a Bitcoin or Ethereum wallet address.

In some embodiments, as part of registering to share private information, the private data providers 101a-101c may receive cryptographic information, such as public and/or private cryptographic keys, that may be used to regulate access secure systems for data sharing. For example, the private data providers 101a-101c may receive, during registration, a public cryptographic key that corresponds to a private cryptographic key held in the execution environment 111. That private cryptographic key may be used to secure the private data, while the public cryptographic key may be shared with those who are granted access to the private data following securing, to enable access.

Accordingly, in some embodiments, as part of registering to share private data, the private data providers 101a-101c may store private data in a data store 107, which may be one data store for all providers 101a-101c, or may be different data stores. The data store 107 may be any suitable repository, such as a database (of any suitable format) and/or a private or public a distributed file system.

An example of a repository for private data is described with reference to FIG. 6. In some embodiments, a private data provider (e.g., one or more of 101a-101c) may store private data locally, on a device operated by the private data provider (the device that executes the distributed application) or on a device on a same network (e.g., an enterprise network) as a device operated by the private data provider. In other cases, the data store 107 in which the provider 101a-101c stores the private data may be a data store outside the direct control of the provider, such as publicly-available data store associated with an operator of system 100.

To help keep data stored in the data store 107 private, the private data providers 101a-101c may cause the private data to be encrypted prior to storage in the data store 107. In accordance with embodiments described herein, the private data may be securely communicated to a secure execution environment 111, which may create the public and private keys from a seed. The seed may be, for example, received from a data provider as part of registration and may be alphanumeric content, such as a set of words or phrases, or other content. The execution environment 111 may secure the data using the private key, such as by encrypting the data. The execution environment 111 may then return the secured data for storage in the data store 107 and return the public key. The secure execution environment 111 may maintain the private key in a secure manner, as discussed below. Subsequently, the secured data and the public key may be provided to the execution environment 111 to decrypt and manipulate the unsecured data. Further details regarding the execution environment 111 are provided below.

When private data is secured and registered in the system 100, one or more records may be created with API service 105, which in the case that the API service 105 is implemented at least in part as a distributed ledger system, may include recording one or more transactions with a distributed ledger. For example, as discussed in more detail below, information regarding the secured execution environment 111 that secured the private data may be stored in a distributed ledger. Such information, as discussed in more detail below, may demonstrate the security of the execution environment 111 and allow for audit of the security. Additionally or alternatively, a smart contract may be recorded with a distributed ledger (the same ledger or a different ledger), that indicates actions to be taken when a private data provider grants access to the private data, examples of which are described in more detail below.

The private data made available for sharing by the providers 101a-101c may be utilized by a private data user for an application. Such an application may use the private data to complete a task, such as a research task. In some cases, the task may be training a model using a volume of private data. Such a model may be, for example, a genomic model for predicting disease risk based on genomic data.

Application provider 109 may, to make use of the private data, submit to the system 100 executable instructions (e.g., software) for executing an application using shared private data. In some embodiments, the application may include an executable program, such as a binary program file. As a non-limiting example, applications may be configured for a range of research tasks including, but not limited to, GWAS models, statistical models, deep learning, machine learning (e.g., neural networks, random forests, logistic regression, and/or other techniques), and/or any other suitable research task. In some embodiments, applications may operate (e.g., for training purposes) on private data sequentially on one or more TEEs (e.g., 211) and/or by accessing batches of private data on a single TEE (e.g., 211). In some embodiments, application outputs may be limited (e.g., to a certain number of bytes) to provide security and prevent private data theft in the output of a malicious model.

In some embodiments, one or more virtual machines may operate in the execution environment 111 to interpret and/or execute the instructions of the application. This may be done such that, when the application processes the private data in an insecure form, the private data is only in an insecure state within the secure execution environment.

Accordingly, in some embodiments, to increase secure, the application (e.g., a binary file for the application) may be audited prior to execution, for example to ensure that the application will not execute malicious code that violates the security of the execution environment and/or steals or otherwise misuses private data. In some embodiments, the application may be configured as a series of instructions for execution by processing circuitry in an execution environment. In some such embodiments, the application provider 109 may only be permitted to choose from a limited set of instructions or instruction modules when developing an application. For example, if an application is to develop a model for a research task, the application may be limited to performing a certain operations on private data as part of training a model. Providing a limited set of instructions may be beneficial over conventional executable files, as it may limit the need to audit executables or other instructions, and make it easier to enforce security policies by limiting how data may be used.

In some embodiments, an application provider 109 may interact with the API service 105 to register an application for processing private data that has been shared in the system 100. In embodiments in which the API service 105 is implemented as a distributed ledger (e.g., as a form of blockchain), application provider 109 may submit to the API service 105 one or more smart contracts corresponding to the application. For example, smart contracts may be added to a distributed ledger (e.g., the Ethereum network blockchain) and may specify conditions under which private data is to be shared with the application. Such conditions may include a method of determining value of the private data submitted to the application, a method of remunerating contributors of the private data that is submitted to the application, and/or other conditions. In embodiments in which the application is to be executed within a secure execution environment 111, such as by a virtual machine executing within the secure execution environment, the application provider 109 may also may also publish information identifying the secure execution environment. Such identifying information may include a network address and/or public cryptographic key, corresponding to an execution environment 111 that hosts the application and/or receives private data.

As discussed in more detail below, in some embodiments, each private data provider 101a-101c may be able to regulate which applications have access to the private data shared by that provider. In some cases, the provider may select, via the distributed application executing on the provider's device, a research task or other application to which to contribute private data. When selected, a transaction may be recorded with a private ledger, indicating that the private data is to be shared with the particular application at the time. As part of recording the transaction, a smart contract may be executed that corresponds to the private data for the data provider. The smart contract may, as discussed above, indicate actions to be taken when access is granted to private data. For example, when access is granted, an identifier for the particular secure execution environment 111 that secured the data (as, in some embodiments, there may be multiple different secure execution environments) may be transmitted to the application provider 109, as well as the public key for the secured private data. Additionally, in some embodiments, an identifier for the data store 107 that is storing the secured private data may be shared with the application provider 109, such that the application provider 109 may retrieve the secured private data such that the private data can be supplied to the secured execution environment 111 for processing. In other embodiments, the smart contract may trigger transmission of the secured private data to the secured execution environment 111. The application may then be transmitted to that secured execution environment 111 with the public key, and the secured execution environment may decrypt the secured data within the secured execution environment 111 and run the application within the secured execution environment 111. Doing so allows the application to execute on the data and, in cases in which the application trains a model, the model to be trained, while still ensuring that the private data is secured and only accessed within the secured execution environment.

The secure execution environment 111 may, in some embodiments, be a trusted execution environment (TEE), which may be one or more cryptographically secure remote computing devices. For example, an execution environment 111 may utilize a pool of processors or other execution environments. An exemplary TEE is described with reference to FIG. 10. As an example, Intel Corporation® Software Guard Extensions (Intel® SGX) or ARM® TrustZone may be used to provide a TEE that allows for data to be operated on securely within the TEE without granting visibility to the data outside the execution environment 111. In some embodiments, the execution environment 111 may only run audited instructions and/or secure virtual machines that limit operations to ensure security and isolation policies.

In some embodiments, as discussed above, to ensure that the execution environment 111 may be trusted, "attestations" that demonstrate the security provided by the execution environment, such as by validating the identity and/or security of the TEE, may be published to a distributed ledger. For example, the TEE may be audited in any suitable manner. The attestations may include any suitable identifier of the execution environment 111 and/or proofs of security. Once a private data provider 101a-101c or private data user establishes a trusted relationship with the execution environment 111 using an attestation, private data may be secured by encrypting the private data using the encryption key for the TEE.

In some embodiments, an application may also be stored in a secure manner within system 100 and access to the application may be regulated using API service 105. For example, in a case in which an application trains a model using private data, the trained parameters of the private model may be treated as private data within a system and may be secured by a secured execution environment 111.

Such an embodiment may be advantageous in scenarios in which an application, once trained, will be run with private data that may be secured using the system 100. For example, if a model is trained for a research task using private data for some members of a population, once trained, private data for a particular other member of the population may be analyzed with the trained model to generate a result. In a case in which a model is trained to identify relationships between genomic data and medical conditions, for example, the model may be subsequently applied to genomic data for a patient under the care of a clinician, to assist the clinician in diagnosing or otherwise treating the patient. By executing within a trusted execution environment, the private data for this other person may be secured, as well.

In such embodiments, once an application has been uploaded to an execution environment 111, an application client 113 may access to the application, such as by purchasing access. For example, a company may want to securely operate on consumer financial records, determine whether a sequence of genomic data is likely inauthentic, and/or operate on genomic data obtained from customers in order to provide additional services beyond sequencing. As another example, an individual may submit private data to be analyzed by an application such as to identify a risk of experiencing a medical condition. The application client 113 may submit payment to the payment system 115 for access to the application. The payment system may specify an amount of remuneration to provide for each private data provider 101a-101c based on the sharing conditions established when the private data providers 101a-101c agreed to share private data.

In some embodiments, payment system 115 may be implemented using a distributed ledger. It should be appreciated that some distributed ledger implementations, such as the Ethereum network, may be used to publish smart contracts as well as cryptocurrency, which may be used as payment. In some embodiments, private data users may create application tokens (e.g., Ethereum Request for Comment 20 (ERC20) compliant tokens) that are associated with one or more applications and provided in exchange for private data. These application tokens may be used to distribute payment received for access to applications, for example by distributing received payments for access according to the number of tokens held by each private data provider 101a-101c. In some embodiments, payments for access to an application may be directly divided among all or a portion of the private data providers 101a-101c, for example as may be governed by a smart contract.

Figure 2:
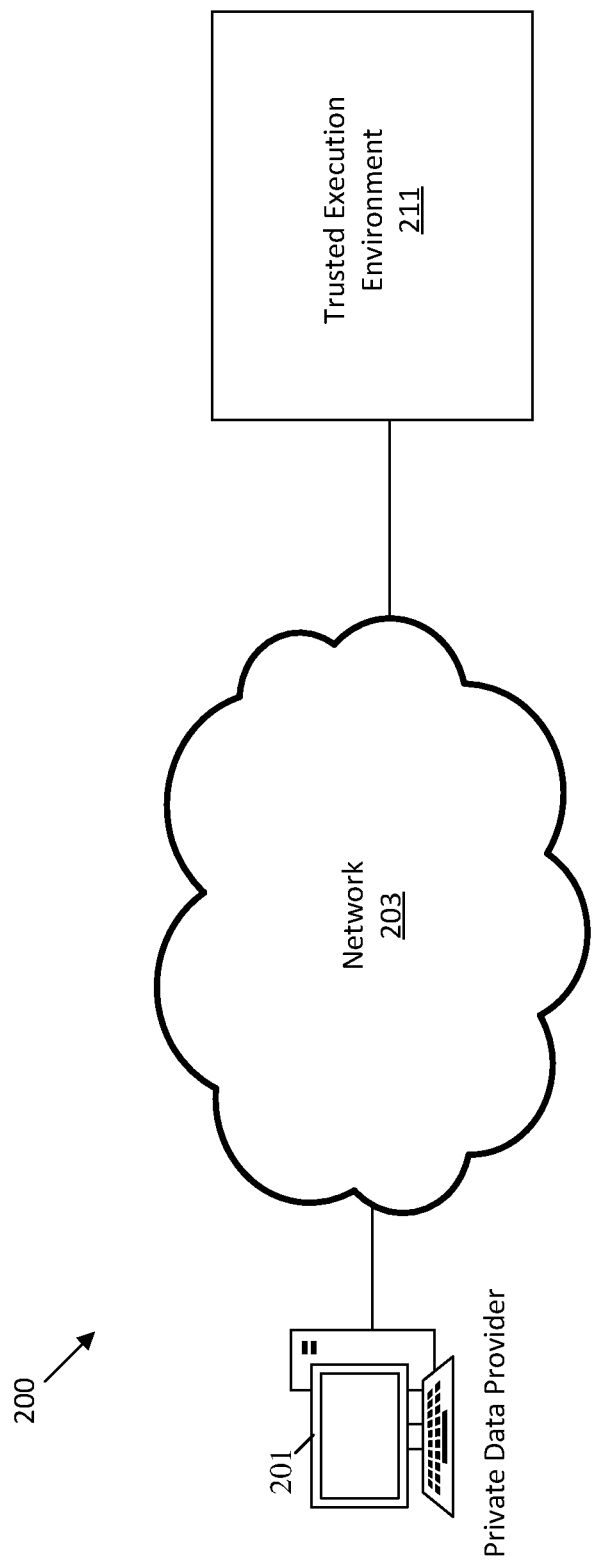
FIG. 2 shows an illustrative diagram of computing devices for providing private data to a trusted execution environment.

FIG. 2 shows an illustrative diagram of computing devices for providing private data to a trusted execution environment 211. The private data provider 201 may transmit private data over the network 203 to the trusted execution environment 211, for example as was described with reference to FIG. 1. In some embodiments, the private data may be encrypted prior to transmission to the TEE 211 and decrypted within the TEE 211. The TEE 211 may operate as was described with reference to execution environment 111 in FIG. 1. In some embodiments, the TEE 211 may be configured to perform a particular purpose, such as processing private data from newly registered users. In some embodiments, a particular virtual machine on the TEE 211 may be isolated from private data users.

In some embodiments, the TEE 211 may be configured to assist with registration of private data by performing various operations on the private data that is being newly added to the system, for sharing. The TEE 211 may perform a variety of registration operations, including encryption of the private data, as embodiments are not limited in this respect.

In some embodiments, the TEE 211 may be configured to perform search indexing on received private data and provide information indicative of characteristics of the private data to the private data user 201. For example, the TEE 211 may compute hashes of portions of the private data to allow for search of the hashes to find private data having desired characteristics. For example, in a case that the private data is genomic data, the genomic data may be indexed based on nucleotides included in the genomic data at particular SNPs or combinations of SNPs, which may be indicative of a particular phenotype characteristics of the individual to whom the genomic data relates.

In some embodiments in which the private data is genomic data, the TEE 211 may be configured to, as part of processing received private data, detect whether genomic data is likely to be inauthentic. Genotype data may be considered authentic when the data represents naturally occurring DNA that was generated by/from an alleged source. In some embodiments, genotype data may be inauthentic when the data is, for example, randomly generated, from a source other than the alleged source (e.g., from a different person or a different species), or otherwise not authentic genotype data. A process for detecting inauthentic data may be performed in a variety of manners. FIGS. 3A-G show illustrative processes that may be used, individually or in combination, to determine whether received genomic data is authentic. The processes may be performed, in some embodiments, by software executing within a trusted execution environment (e.g., 111, 211, and/or 1011).

Figure 3A:
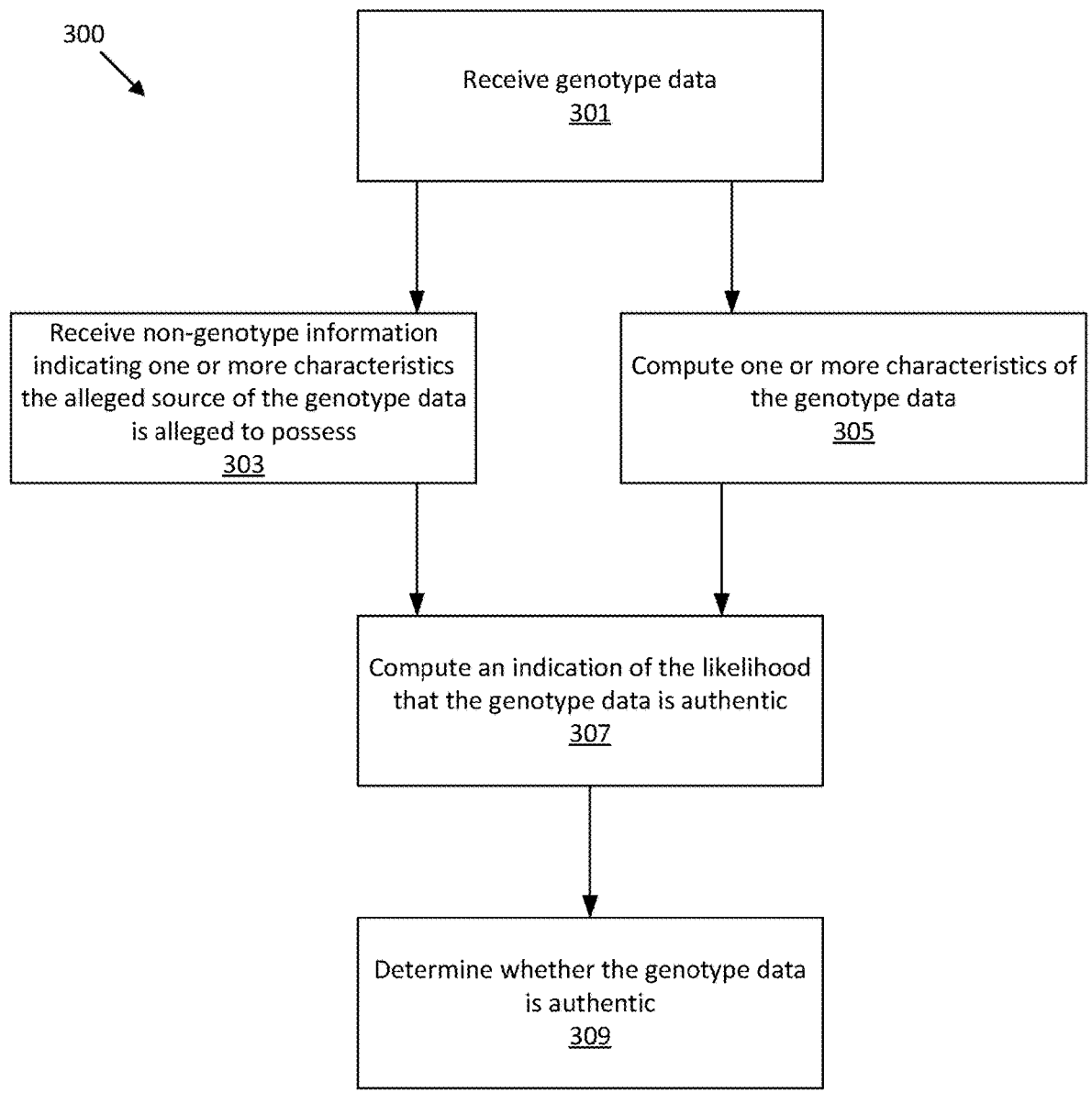

FIG. 3A shows an illustrative process 300 for determining whether genomic data that is alleged to be associated with a person is authentic, which leverages both the genomic data and non-genomic data, both of which are alleged to relate to the person.

The process 300 of FIG. 3A beings at act 301, in which genotype data is received. Genotype data may be received from a private data provider, such as was described with reference to FIG. 1. To determine whether the genotype data is inauthentic, the process flow may proceed to only one or both of act 303 and act 305.

At act 303, non-genotype information is received that indicates one or more characteristics that the alleged source of the genotype data is alleged to possess. In some embodiments, the non-genotype information is self-reported from the private data provider. For example, the private data provider may provide non-genotype information through a suitable user interface. The non-genotype information may include, but is not limited to, any or all of a biological sex, an ethnic ancestry, and one or more phenotypical characteristics.

At act 305, one or more characteristics of the genotype data are computed. In some embodiments, a measure of correlation between SNPs in the genotype data may be computed. In authentic DNA, linkage disequilibrium (LD) measures natural correlations between nucleotides at certain SNPs. Thus, the inventors have recognized that LD values may be computed to indicate the correlation between nucleotides of certain SNPs to distinguish authentic genotype data from inauthentic genotype data. In some embodiments, the LD values may be an $r^2$ statistical value.

At act 307, an indication of the likelihood that the genotype data is authentic (and/or inauthentic) is computed. In some embodiments, for any or all of the characteristic received at act 303 and/or computed at act 305 genomic data commonly associated with the characteristic may be obtained, for example from a database or genomic study related to the characteristic. In such embodiments, for each characteristic of the one or more characteristic, it may be determined whether at least a part of the genomic data matches the genomic data commonly associated with the characteristic. To make the determination, a characteristic may be inferred from the genetic data for any or all of the characteristics, and the inferred characteristic may be compared to the received and/or computed characteristics. In some embodiments, the comparison may be used as the basis for computing a probability or other indication of the likelihood that the genotype data is authentic.

At act 309 it is determined whether the genotype data is authentic. For example, in some embodiments, the indication of the likelihood that the genotype data is authentic is compared to a threshold.

Figure 3B:
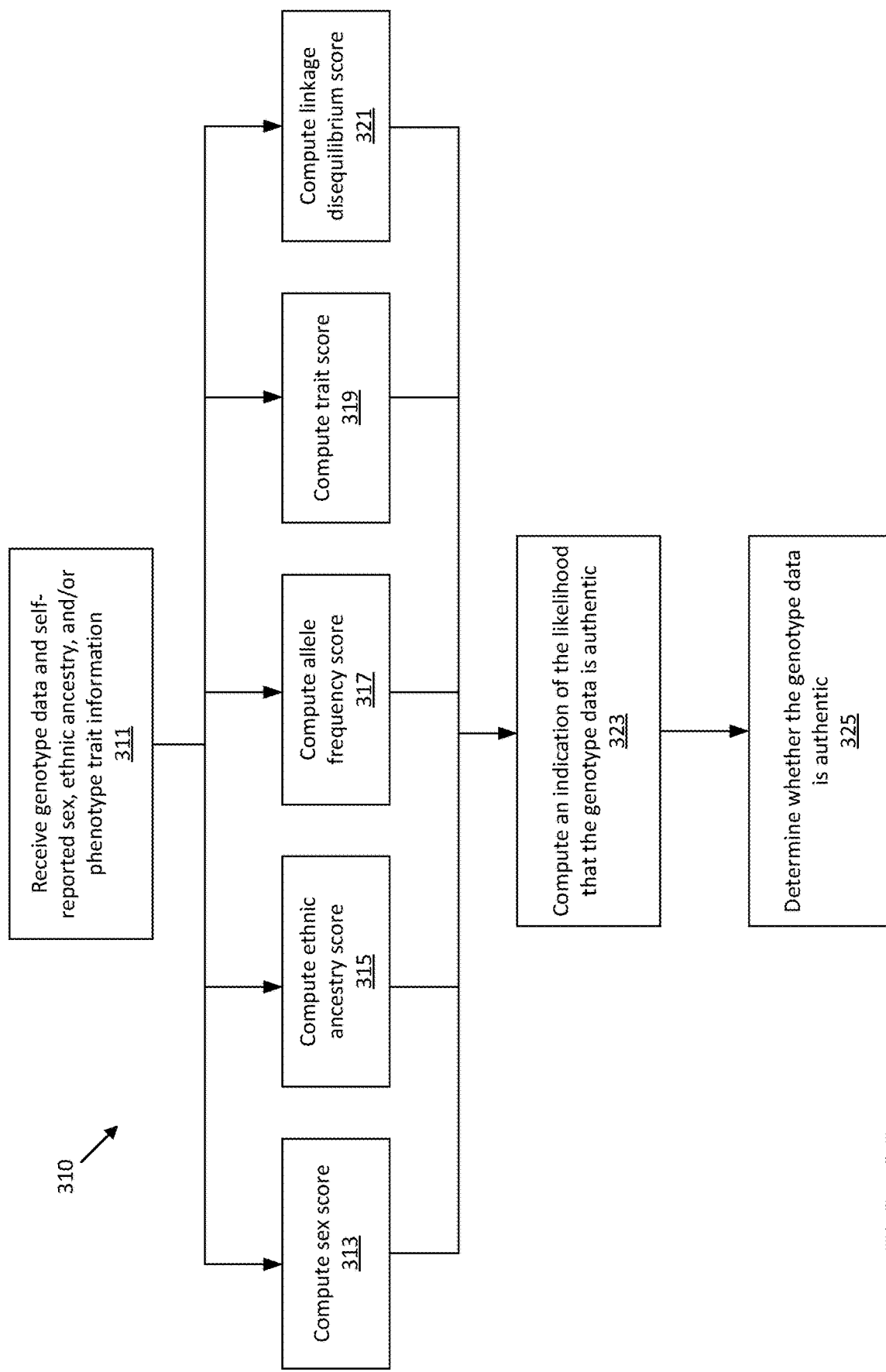

FIG. 3B shows an illustrative process 310 for determining whether genomic data is authentic that includes calculation of a number of scores, which may provide a quantitative value indicative of some of the factors discussed above in connection with FIG. 3A. The process 310 of FIG. 3B may generate a quantitative likelihood that genotype data is authentic.

The process 310 begins at act 311, in which genotype data is received from a private data provider along with one or more of a self-reported biological sex, ethnic ancestry, and/or phenotypical characteristic information that is alleged to be for the person to which the genotype data relates.

At act 313, a sex score is computed based on the genotype data and on the received biological sex. An example of a manner in which a sex score may be computed is described below with reference to FIG. 3C.

Figure 3C:
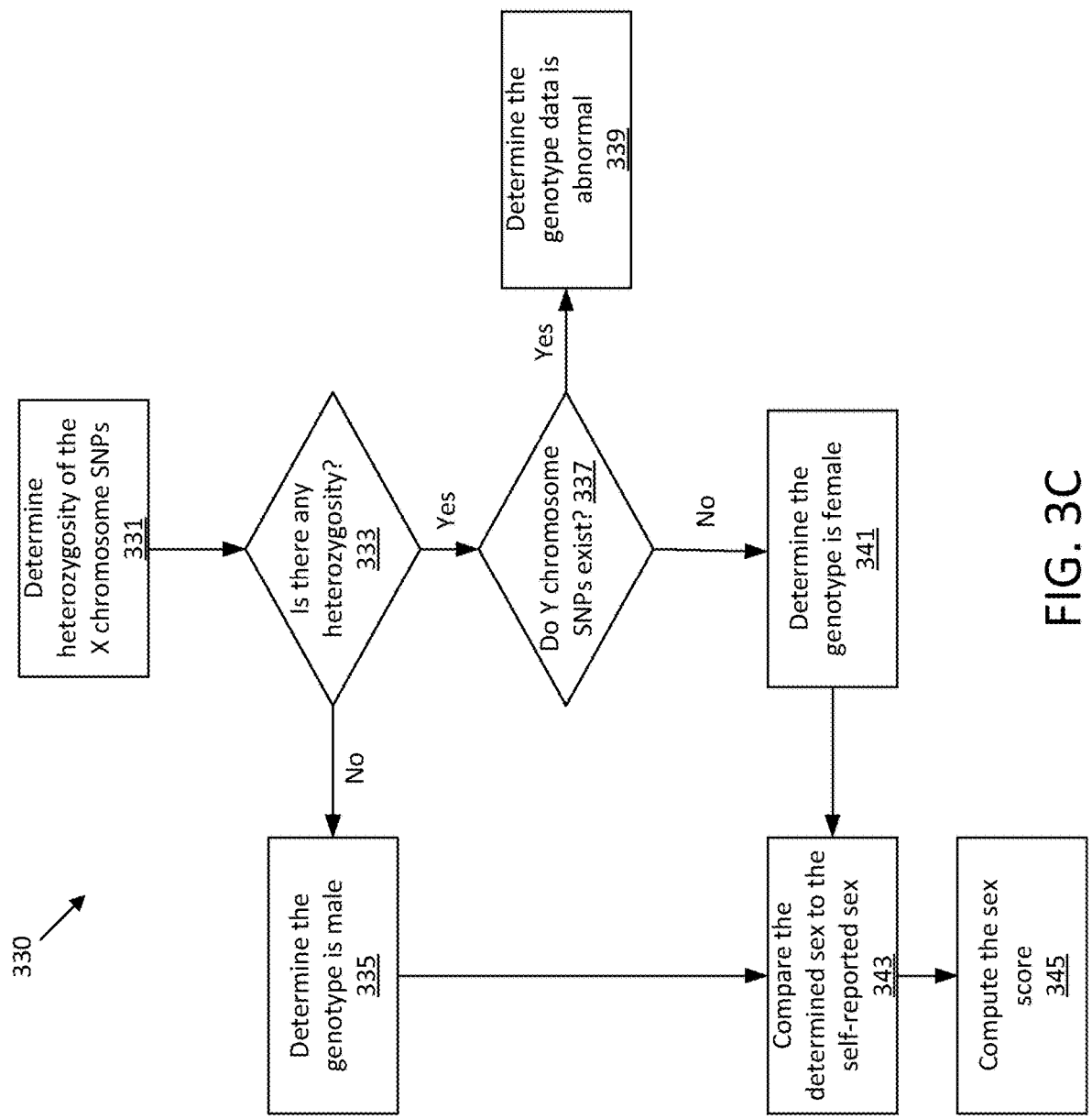

FIG. 3C illustrates a process 330 for determining whether received genotype data corresponds to received phenotype information indicating biological sex. That is, whether the genotype data indicates the same sex that a user input for the person to whom the genotype data supposedly relates.

The process 330 of FIG. 3C beings at act 331, in which a heterozygosity of the X chromosome SNPs of the input genotype data is determined. For example, the nucleotides at multiple SNPs on the X chromosome may be compared. At act 333, it is determined whether there is any heterozygosity in the genotype data (e.g., different nucleotides at at least one SNP). If not, then the genotype data is homozygous and, at act 335, it is determined that homozygosity indicates that the true genotype source only has one X chromosome and therefore corresponds to a male.

If, however, it is determined at block 333 that there is heterozygosity in the X chromosome data of the genotype data, then at act 337 it is determined whether the genotype data includes any Y chromosome SNPs. If there are Y chromosome SNPs present, it is determined at act 339 that the genotype data is abnormal. This is because heterozygous genotype data that also includes a Y chromosome is uncommon. This may be a sign that the genotype data is not authentic, or may be a sign that the person to whom the genotype data corresponds has unusual genotype data.

If it is determined in act 337 that No Y chromosome SNPs are included in the genotype data, then in block 341 it is determined that the genotype data corresponds to a female.

At act 343, the received biological sex is compared to the inferred biological sex. Based on the comparison, and at act 345, the sex score is computed. The sex score may be based on a conditional probability of observing the inferred sex of the genotype data given the received sex.

In some embodiments, a likelihood of incorrect reported sex may be quantified using SNP data in openSNP database (available at https://opensnp.org/version2016-04-27), which allows volunteers to upload DNA and phenotype data to contribute to scientific research. In some embodiments, a conditional probability may be derived as follows:

$$\text{Prob}(\text{self\_reported sex} \mid \text{DNA is authentic}) = \begin{cases} 89\% & \text{self\_reported} = \text{inferred} \\ 11\% & \text{Unmatch} \end{cases}$$

A sex score for use in inauthentic DNA detection may be a corresponding log conditional probability:

$$\text{Score}_{sex} = \log(\text{Prob}(\text{self\_reported sex} \mid \text{DNA is authentic}))$$

In some embodiments, using log probability instead of the raw probability may yield benefits in combining the sex score for scores for other factors. Such benefits may include mathematical simplicity, as it may be easier in some contexts to combine scores using summation of log probabilities than multiplication for small numbers, as may be used instead if the scores were calculated as probabilities rather than log probabilities. Using log probabilities may also avoid numerical error for multiplication of small numbers, which may arise when probabilities are used.

Returning to FIG. 3B, at act 315, an ethnic ancestry score may also be computed based on the received ethnic ancestry. An example of an approach to computing the ethnic ancestry score is described with reference to FIG. 3D.

Figure 3D:
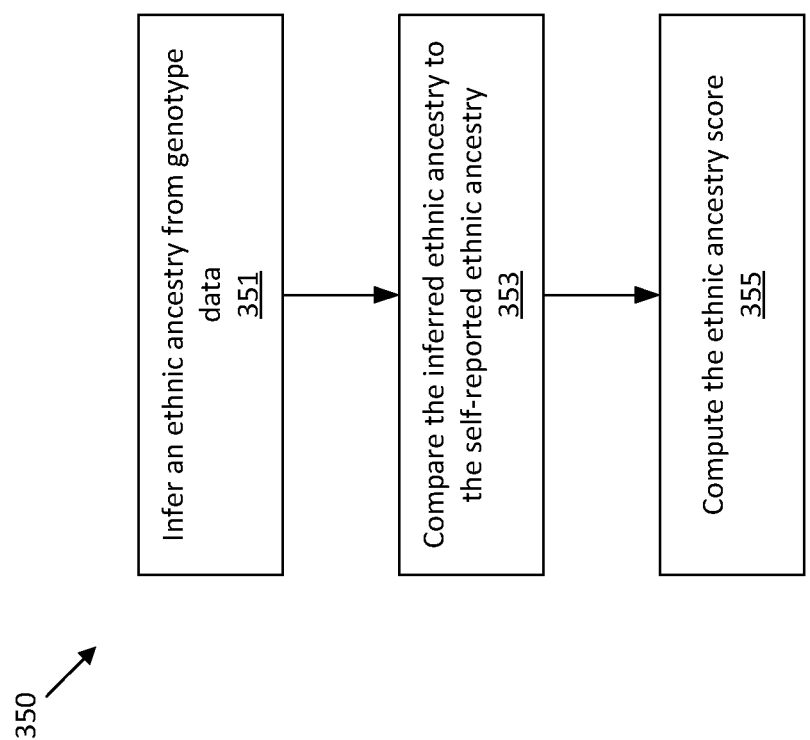

FIG. 3D shows an illustrative process 350 for computing an ethnic ancestry score. At act 351 an ethnic ancestry is inferred from the genotype data. In some embodiments, the ethnic ancestry corresponding to the genotype data may be inferred by extracting ancestry anchor SNPs from the genotype data. The ancestry anchor SNPs may then be used to determine an inferred ethnic ancestry from the genotype data. At act 353, the inferred ethnic ancestry may be compared to the self-reported ethnic ancestry. Based on the comparison, and at act 355, the ethnic ancestry score is computed. The ethnic ancestry score may be based on a conditional probability of observing the inferred ethnic ancestry of the genotype data given the received ethnic ancestry.

As an illustrative example, the following technique may be applied to SNP data to infer ancestry.

First, a smaller number of SNPs (e.g., 600,000, directly measurement from the genotyping Chip assay) from each sample may be imputed to a larger number of SNPs (e.g., 7 million, computational predictions). This may be done in any suitable manner, e.g., using the software Impute2 and 1000 genome project phased 3 reference panel. Because the nearby SNPs are usually co-inherited, the software utilizes the observed co-occurrence relationship among the genotypes of SNP locations from large population data with whole genome sequencing (1000 genome project), and infer the genotypes of unmeasured SNP locations from the nearby SNP with the direct measurements.

Second, a number of ancestry anchor SNPs (e.g., 162645) may be extracted from the imputed SNPs. This may be done in any suitable manner, e.g., according to https://github.com/Ancestry/cehg16-workshop. This workshop describes how to apply the software Admixture to infer one person's ancestry using his/her DNA genotype data.

Third, the ancestry anchor SNPs may be input to Admixture software, which may output an inferred ancestry. The software builds ancestry model from large ancestry labeled DNA genotype data, and once the ancestry model was built, and the software uses the model to assign an ancestry label to new genotype data.

In some embodiments, ancestry matching (e.g., using the illustrative steps described above) may be used either alone, or in combination with other techniques, to detect inauthentic DNA data. For instances, a sample for which inferred ancestry does not match self-reported ancestry may be flagged as a potentially inauthentic DNA sample.

For instance, the illustrative steps described above may be applied to DNA data in the openSNP database. In one experiment, 23andme SNP data available in the openSNP database was used. There were 64 samples with self-reported ancestry as "Northern European." (The "Northern European" population had the largest number of samples in the openSNP database at the time the experiment was conducted.) The illustrative steps described above were applied to each of the 64 samples. The inferred gender output by the Admixture software was "Finnish" for 59 out of the 64 samples. ("Finnish" is the closest available label to "Northern European.") Thus, in this experiment, inferred ancestry matches self-reported ancestry in 92% of the samples.

In some embodiments, a conditional probability may be derived as follows:

$$Prob(\text{self\_reported ancestry} \mid DNA \text{ is authentic}) = \begin{cases} 92\% & \text{self\_reported = inferred} \\ 8\% & \text{Unmatch} \end{cases}$$

An ancestry score for use in inauthentic DNA detection may be a corresponding log conditional probability:

$$Score_{ancestry} = \log(Prob(\text{self\_reported ancestry} \mid DNA \text{ is authentic}))$$

Returning to FIG. 3B, at act 317, an allele frequency score may be computed based on the received ethnic ancestry. The computation of the allele frequency score is described with reference to FIG. 3E.

FIG. 3E shows one illustrative process 360 that may be used for computing the allele frequency score. At act 361, the probability of observing a plurality of alleles in the genotype data is determined based on the received ethnic ancestry information. At act 363, the probability of observing a plurality of nucleotides in the genotype data based on the conditional probabilities is determined. At act 365, an allele frequency score is computed based on the probability computed in act 363.

The inventors have recognized and appreciated that given the allele frequency of different SNPs in a population, one can compute the likelihood of genotypes that are natural derived from the population. Therefore, if the likelihood is low, it indicates the number of SNPs carrying relatively rare allele is unexpectedly high, which could indicate inauthentic DNA data.

Accordingly, in some embodiments, an "allele-frequency score" ($Score_{allele\_freq}$) may be computed for an uploaded DNA sample. This score may measure average consistency of observed genotypes to allele frequency in a population. Thus, a low $Score_{allele\_freq}$ for a given sample may indicate that the sample is likely inauthentic.

In some embodiments, given self-reported ancestry information, a conditional probability of observing a genotype dose $d_i$ for the $i^{th}$ SNP may be calculated as follows.

$$Prob(\text{genotype dose } d_i \mid \text{ancestry}) = (1-f_i)^{2-d_i} * f_i^{d_i}$$

In this example, $d_i$ denotes a dosage of the $i^{th}$ SNP. For instance, if both alleles observed from that SNP are the minor allele in a population, then the dosage may be 2. If that SNP is heterozygous, then the dosage may be 1. If that SNP is homozygous with the major allele in the population, then the dosage may be 0.

Also, in this example, $f_i$ denotes a minor allele frequency of the $i^{th}$ SNP in the given population. The minor allele frequency may be obtained in any suitable manner, for example, from the 1000 genome project.

The inventors have recognized and appreciated that, population allele frequency may have limited precision (e.g., due to limited sample size). Accordingly, in some embodiments, allele frequency below 0.001 may be replaced by the constant value 0.001 to avoid numerical issues. Thus, an allele frequency score may be computed as follows, where N is the number of SNPs in an uploaded sample.

$$Score_{allele\_freq} = \frac{\sum_{i=1}^{N} \log(Prob(\text{genotype dose } d_i \mid \text{ancestry})) - 2*\log(0.5)}{N}$$

The inventors have recognized and appreciated that an allele-frequency score such as the one computed above may represent an average log probability of observed genotype doses. In the above example, the constant terms "2*log (0.5)" may shift the score with mean 0. It should be appreciated that aspects of the present disclosure are not limited to the use of any constant term.

In one experiment, openSNP database genotype samples are used to compute allele-score distributions. For instance, a first distribution is computed for original samples (which are assumed to be authentic), and a second distribution is computed for inauthentic samples obtained by randomly mutating 10% of the SNPs. The results, shown in FIG. 7 below, indicate that an allele frequency score, such as $Score_{allele\_freq}$ as described above, may be used to distinguish between authentic DNA samples (green) and inauthentic DNA samples (red).

Returning to FIG. 3B, at act 319, a trait score may be computed based on the received phenotypical traits. The computation of the trait score is described with reference to FIG. 3F.

Figure 3F:
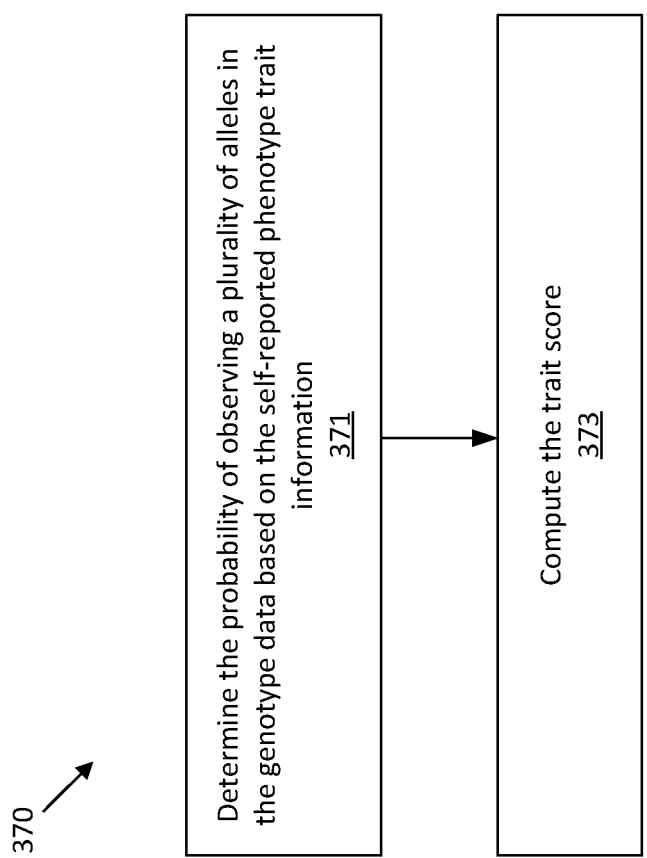

FIG. 3F shows one illustrative process 370 that may be used for computing a trait score to be used to determine whether genotype data is authentic.

At act 371, the probability of observing a plurality of nucleotides at certain alleles in the genotype data is determined based on the self-reported phenotypical trait information. At act 373, the phenotypical trait score is computed based on the determined probabilities.

The inventors have recognized and appreciated that certain body features such as eye color, hair color, and cleft chin are highly heritable (Heritability measure $H^2>0.7$), and therefore predictable from DNA genotyping data, which means the common variants instead of rare variants contribute to those phenotypes. Accordingly, in some embodiments, matching of one or more traits (e.g., using the illustrative steps described below) may be used either alone, or in combination with other techniques, to detect inauthentic DNA data.

In some embodiments, a score $Score_{trait}$ may be calculated to quantify an extent of matching between self-reported phenotypes and predicted phenotypes on one or more highly heritable traits. This may be done in any suitable manner, for instance, by compute a likelihood of observing a self-reported phenotype using a polygenic risk score model for a trait:

$$\text{Prob}(\text{self\_reported phenotype}|\text{model,DNA data}).$$

The polygenic risk score model generate a risk score of a person given the genotype data across the genome for a particular trait. The polygenic risk score model usually assume the additive effects from different SNPs across genome, and the effect size of each SNP can be estimated from the case-control genetic study for that trait.

A trait score for use in inauthentic DNA detection may be a corresponding log conditional probability $$\text{Score}_{trait}=\log(\text{Prob}(\text{self\_reported phenotype}|\text{model}, \text{DNA data}))$$

Returning to FIG. 3B, at act 321, a linkage disequilibrium score may be computed. The computation of the linkage disequilibrium score is described with reference to FIG. 3G.

Figure 3G:
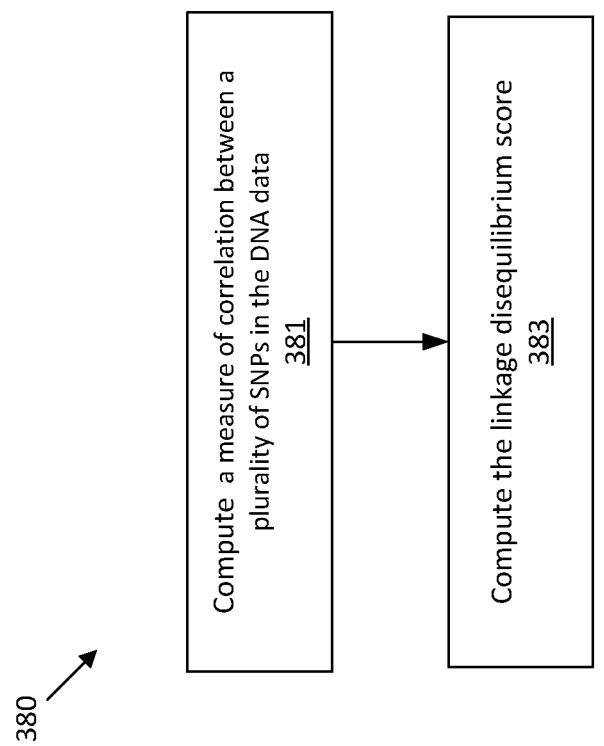

FIG. 3G shows an illustrative process 380 that may be used for computing a trait score to be used to determine whether genotype data is authentic. The process 380 begins at act 381, where a measure of correlation between a plurality of nucleotides in the genotype data is computed. In some embodiments, the measure of correlation includes a likelihood of the received nucleotides co-occurring in the genotype data. In some embodiments, computing the likelihood of the nucleotides naturally co-occurring includes computing a LD correlation for the SNPs. At act 383, a linkage disequilibrium score is computed for the genotype data based on the measure of correlation. LD calculations may be made as is described with reference to FIGS. 4A-D.

Returning to FIG. 3B, at act 323, an indication of the likelihood that the genotype data is authentic may be computed. In some embodiments, all or some of the scores computed in acts 313, 315, 317, 319, and/or 312 are used in computing the likelihood. In some embodiments, the scores are based on logarithms of probabilities are combined by addition. The scores may be combined according to any suitable mathematical formula. In some embodiments, all or a portion of the scores may be input to a statistical classifier to generate a probability of the scores naturally occurring together.

At act 325, it is determined whether the genotype data is authentic, for example by comparing the combined score and/or an indication of the likelihood of the combined score to a threshold.

In some embodiments, a combined score may be calculated for each subject in a validated database, which is assumed to contain authentic data. An empirical $\text{Score}_{combine}$ distribution may be computed for future use of inauthentic DNA detection. For example, the empirical distribution may be calculated as follows.

$$p\text{-value}=\text{Prob}(\text{self-reported attributes}|\text{uploaded SNP genotype is authentic})$$

In some embodiments, a p-value threshold may be selected for rejecting the hypothesis of "uploaded DNA is authentic." For example, if a p-value calculated from self-reported attributes and corresponding uploaded DNA data is less than 0.001, then the uploaded DNA may be flagged as being potentially inauthentic DNA. The choice of p-value thresholds may represent a tradeoff between false positive and false negative. For instance, a lower p-value threshold may lead to lower probability of misclassifying authentic DNA as inauthentic DNA. It may be desirable to use a p-value threshold that is lower than 0.05. However, it should be appreciated that aspects of the present disclosure are not limited to the use of any particular threshold.

As discussed above, in some embodiments, genomic data may be collected to train a model to relate genotype information (e.g., a particular set of nucleotides for particular SNPs) to phenotype information, such as whether a patient has a particular medical condition (e.g., disease). An application may be executed by a trusted execution environment and may analyze genomic data for a particular person to generate a likelihood that that person has a particular medical condition.

Figure 4A:
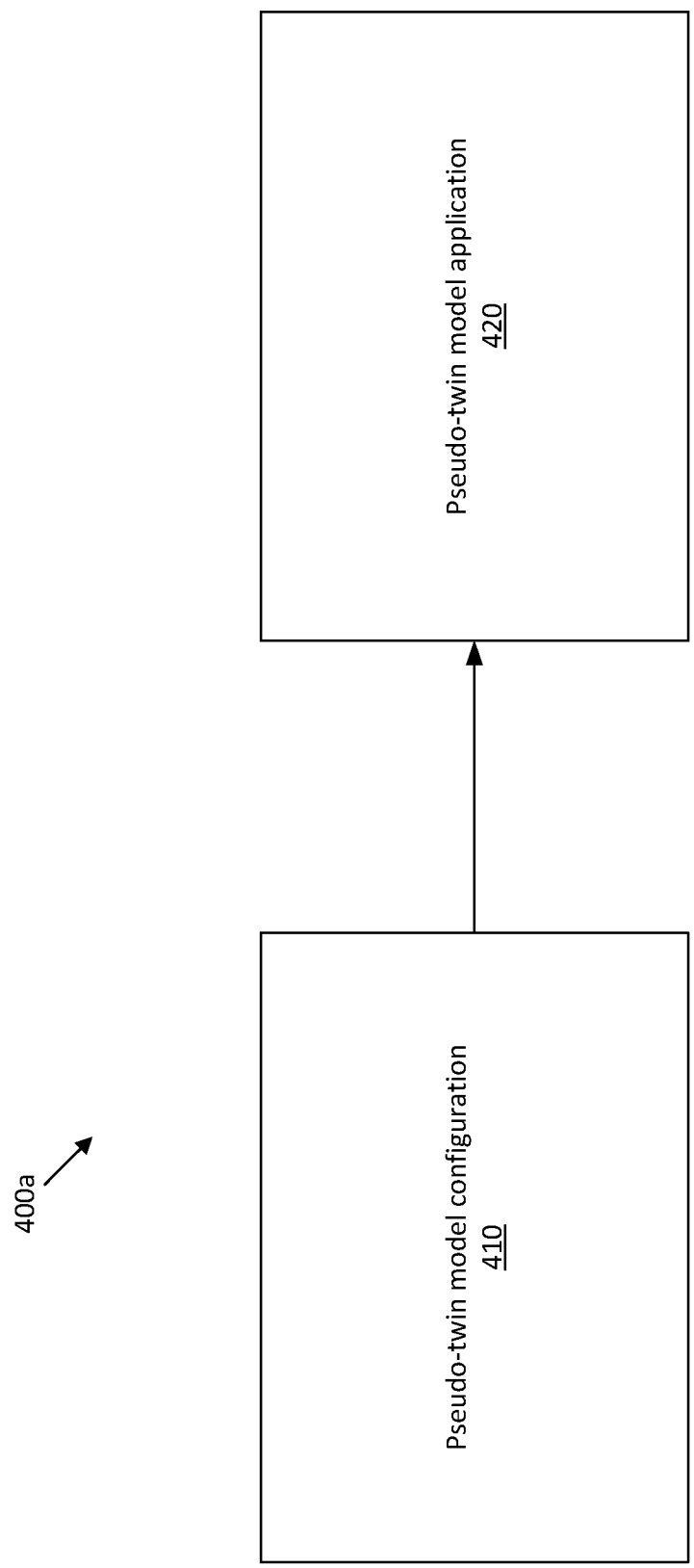
FIGS. 4A-D show illustrative processes for estimating a likelihood that a given person will experience a medical condition.

FIGS. 4A-D show illustrative processes that may be implemented in some embodiments for estimating a likelihood that a given person will experience a medical condition. FIG. 4A shows an illustrative process 400a for estimating a likelihood that a given person will experience a medical condition by configuring and applying a pseudo-twin model.

As discussed above, pairs of individuals from a population who share a same set of condition-risk variants for a given complex disease may be referred to as "pseudo twins." A pseudo-twin model may be configured to receive private genomic data, and corresponding disease diagnoses and/or statuses, from a population of individuals and may estimate a risk of a medical condition for an individual, based on whether that individual's pseudo-twins have the medical condition. For example, the pseudo-twin model may receive genomic data from the individual and compares condition-associated SNPs in the received genomic data to the population data. When the received genomic data exceeds a threshold level of similarity to genomic data in the model, a pseudo-twin is detected. The detected pseudo-twins may then be used to determine the likelihood that the individual will experience the medical condition, based on whether the one or more pseudo-twins have been diagnosed with the medical condition. For example, the proportion of pseudo-twins with the disease may be output as the likelihood of experiencing the disease.

At act 410 a pseudo-twin model is configured, and at act 420 the configured pseudo-twin model is applied to data for individuals (e.g., patients under care of a clinician, being evaluated for whether they may have a medical condition), to identify pseudo-twins and estimate risk. The pseudo-twin model may be configured based on a collection of private data from private data providers. In some embodiments, the private data used to configure the pseudo-twin model may include genotype data and a medical condition status, which may include a diagnosis of having a disease. The pseudo-twin model may be applied to genotype data associated with an individual to determine a risk that the individual will experience a medical condition based on pseudo-twins that are identified in the model.

Figure 4B:
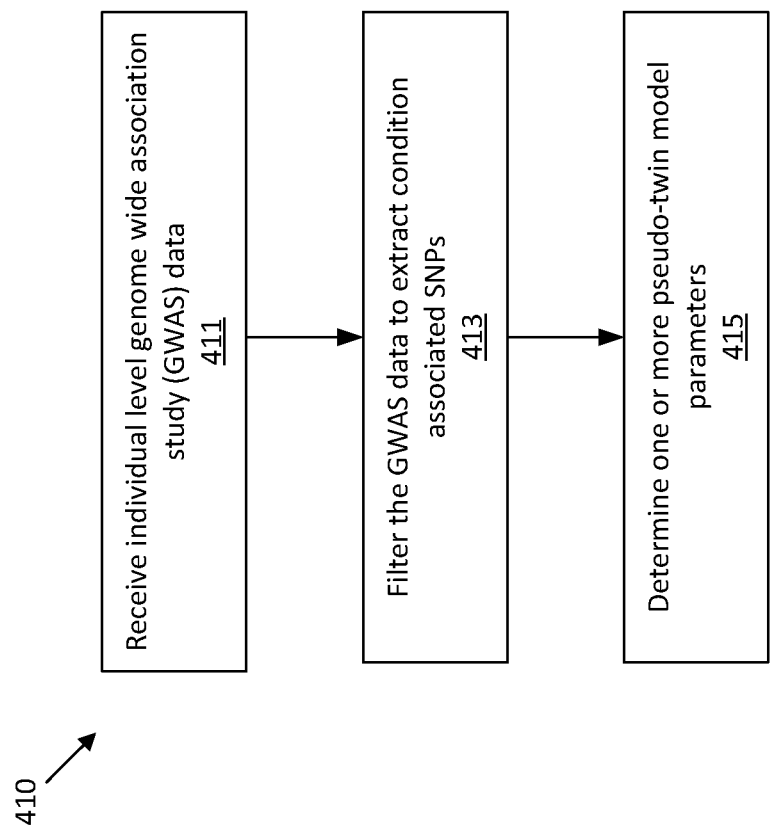

FIG. 4B shows an illustrative process 410 for configuring a pseudo-twin model. The process begins at act 411, where individual level genome wide association study (GWAS) data is received for a population. The GWAS data may be private data received from one or more private data providers and may be received at a TEE, for example as is described with reference to FIG. 1 above and FIG. 7 below.

At act 413, the GWAS data is filtered to extract condition-associated SNPs for a medical condition, which may be a set of SNPs (i.e., base positions) that include information that would be relevant to whether a particular person has a particular medical condition. Different sets of SNPs may be identified as condition-associated for different medical conditions. The filtering process may include identifying, from a large set of SNPs, the SNPs that are relevant or more relevant than others to presence or absence of the medical condition.

Filtering the GWAS data, in some embodiments, may include p-value pruning and/or LD pruning.

In some embodiments, only SNPs for which there is statistical evidence indicating a correlation with the disease (or other medical condition for which the model is being trained) may be considered, which may be referred to as p-value pruning. A genome-wide significance threshold of 5E-8 is commonly used for determining correlation or association, in other contexts. However, the inventors have recognized and appreciated such a stringent threshold may lead to exclusion of all but a small portion of causal SNPs. The inventors have further recognized and appreciated that, for pseudo twin matching, inclusion of more causal variants may be desirable. Accordingly, in some embodiments, more relaxed thresholds may be used (e.g., GWAS p-value cutoff from 1E-7 to 1E-4).

The inventors have recognized and appreciated that, although using a lower threshold may lead to inclusion of falsely associated SNPs (e.g., SNPs not actually relevant to presence or absence of the medical condition), such SNPs may not decrease accuracy in a pseudo twin approach. Instead, a looser p-value cut-off may actually yield higher accuracy in pseudo twin matching in some scenarios.

However, falsely associated SNPs may also increase difficulty in identifying a pseudo twin match for a given individual, if too loose a p-value cutoff is used. For example, if a p-value cut-off of 1 is used, then all SNPs must be matched, and it may be almost impossible to find two matching people who are not monozygotic twins.

The inventors have recognized and appreciated that a cut-off of 1E-6 may represent a good trade-off between accuracy and ability to find matches. However, it should be appreciated that aspects of the present disclosure are not limited to the use of any particular cut-off. For instance, a lower cut-off may be used as more data is gather and it becomes easier to identify matches.

The inventors have further recognized and appreciated that SNPs located nearby a causal SNP in a genome (e.g., within a certain number of base positions of the causal SNP) for a medical condition may also have strong association with that medical condition, as SNPs located proximate to one another may often vary together. The inventors have further recognized and appreciated that it may be desirable to exclude such "extra" SNPs. SNPs that vary together and thus carry almost the same information may have a high chance of passing a p-value threshold together. Once they pass the threshold together, if all SNPs for a given area of the genome, which vary together, are used in training the model, this extra data may introduce bias in the model and in the pseudo twins matching.

Also, including more SNPs in the pseudo-twin identification process may make identification of a pseudo-twin more difficult. As discussed above, a pseudo-twin is identified as someone who has the same or more than a threshold matching number of nucleotides for condition-associated SNPs. Identifying pseudo twins may become difficult when there are more SNPs to consider, as more SNPs may need to be matched to identify members of a population as pseudo-twins. Additionally, when the additional SNPs do not add much information to the model, as their tendency to vary together with other SNPs make the additional SNPs arguably redundant, such increased difficulty is unnecessary and may have limited or no benefit.

Such a tendency for SNPs to vary together may be quantified by measuring linkage disequilibrium (LD) between SNPs. Accordingly, an LD value for a pair of SNPs may be used to determine whether to exclude a SNP from consideration.

In some embodiments, a strength of LD between two SNPs may be measured by an $r^2$ value, which may range between 0 and 1, where $r^2=1$ may indicate implies the two SNPs provide exactly the same information. In some embodiments, $r^2$ may be calculated as follows.

$$r^2 = \frac{P_{AB} - P_A P_B}{P_A(1-P_A)P_B(1-P_B)}$$

In this example, $P_A$ denotes a probability of a first SNP with allele A, and $P_B$ denotes a probability of a second SNP with allele B, and $P_{AB}$ denotes a probability of observing both the first SNP with allele A and the second SNP with allele B.

In some embodiments, ancestry-specific LD $r^2$ statistics for SNPs within 1 Mbp may be used. Such statistics may be obtained in any suitable manner, for example, from the 1000 Genomes Project. The 1000 Genomes Project provides a comprehensive description of common human genetic variations by applying whole-genome sequencing to a diverse set of individuals from multiple populations. The genomes of 2,504 individuals from 26 populations have been reconstructed, including >99% of SNP variants with a frequency of >1% for a variety of ancestries.

In some embodiments, LD pruning may be performed as follows. First, a most significant SNP associated with a disease may be selected based on GWAS p-value. All nearby SNPs (e.g., within 1 Mbp of the selected SNP) with an $r^2$ value above a selected LD threshold may be removed, where the $r^2$ value is computed between the selected SNP and the SNP that is being considered for removal.

In some embodiments, an LD threshold of $r^2>0.8$ may be used, but it should be appreciated that aspects of the present disclosure are not limited to the use of any particular LD threshold. For instance, the inventors have recognized and appreciated that a lower LD threshold may lead to fewer selected SNPs may improve the likelihood of finding a pseudo twin, but may prune out some true causal SNPs.

In some embodiments, after performing LD pruning based on a most significant SNP, a next most significant SNP in the remaining SNPs may be selected, and LD pruning may be performed based on the next most significant SNP. This may be repeated until a next most significant SNP in the remaining SNPs no longer satisfies a selected GWAS p-value cutoff (e.g., as described above in connection with p-value pruning)."

At act 415, one or more pseudo-twin model parameters may be determined. For example, a threshold for a level of similarity between genotype data to determine that two samples correspond to pseudo-twins may be determined.

Figure 4C:
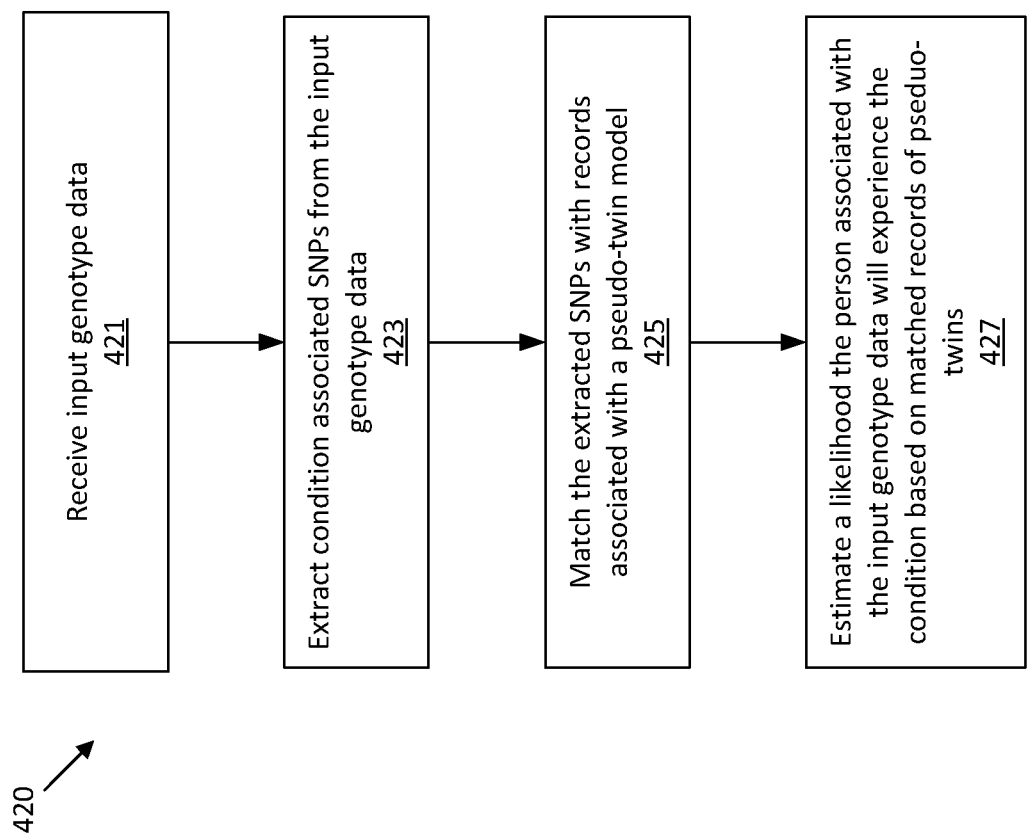

FIG. 4C shows an illustrative process 420 for applying a pseudo-twin model. The process 420 begins at act 421, where input genotype data is received. The input genotype data may be received from a private data provider and correspond to an individual. The pseudo-twin model may be operable to determine a risk of the individual will experience one or more medical conditions. At act 423, condition associated SNPs are extracted from the input genotype data.

The condition associated SNPs may have been determined by the GWAS filtering and model configuration described with reference to FIG. 4B.

At act 425, the extracted SNPs are matched with records associated with the pseudo-twin model. In some embodiments, a query individual may be matched to one or more individuals in a database with respect to a set of SNPs selected for a disease. For instance, a query may be constructed as a K-dimensional vector $x=g^K|g\in\{0,1,2\}$, where K is the number of selected SNPs and the values 0, 1, 2 represent genotypes of each selected SNP. For instance, homozygosity reference allele may be represented by 0, heterozygosity may be represented by 1, and homozygosity alternative allele may be represented by 2. In some embodiments, the reference allele and the alternative allele for each SNP may be defined according to the 1000 Genomes Project and hg19 version of human reference Genome.

In some embodiments, genotype records in a database may be extracted for the K selected SNPs, and represented as a set of K dimensional vectors $\{y=g^K|g\in\{0,1,2\}|y$ in database$\}$. Given a query vector x and record vectory, similarity between the two vectors may be calculated as a percentage of dimensions that are identical, as follows.

$$\text{Similarity} = \frac{\sum_{i=1}^{K} x_i == y_i}{K}$$

In some embodiments, a high level of similarity between a query vector x and data vectory may be required to classify the query individual and the record individual as pseudo twins for a given disease. Experimental results suggest that high prediction accuracy may be obtained when a high similarity threshold is used (e.g., >0.9).

In some embodiments, a similarity threshold for a given disease may be determined by testing different candidate threshold values (e.g., from 0.9 to 1) and selecting a threshold value with a highest concordance rate.

In some embodiments, a concordance rate for a candidate threshold values may be calculated as the percentage of pairs in which both individuals have the disease of interest, out of all pairs in which at least one individual has the disease, where each pair include two individuals in a database that are deemed to be matching according to the candidate threshold. The concordance rate may be calculated only if there are at least three pairs of individuals with similarity above the candidate threshold, which may provide a better indication of model performance. However, that is not required, as in some embodiments concordance rate may also be calculated if there are two or fewer pairs with similarity above the candidate threshold.

At act 427, a likelihood that the individual associated with the input genotype data will experience the condition based on matched records of pseudo-twins. In some embodiments, a given query individual may be matched to one or more individuals in a database with respect to a given disease (e.g., as described above). Disease risk of the query individual may then be calculated as a percentage of the query individual's pseudo-twins with the disease.

$$\text{disease risk} = \frac{\text{\#pseudo twins with disease}}{\text{\#pseudo twins}}$$

In some embodiments, a variance of the disease risk estimation may be reported. For instance, a variance may be derived from a variance of concordance rate µ for pseudo-twin pairs in the database for that disease of interest.

$$\text{var(disease risk)}=\mu(1-\mu)$$

The concordance rate µ may be the percentage of matching pseudo-twins having the same disease/trait status as the query person.

Figure 4D:
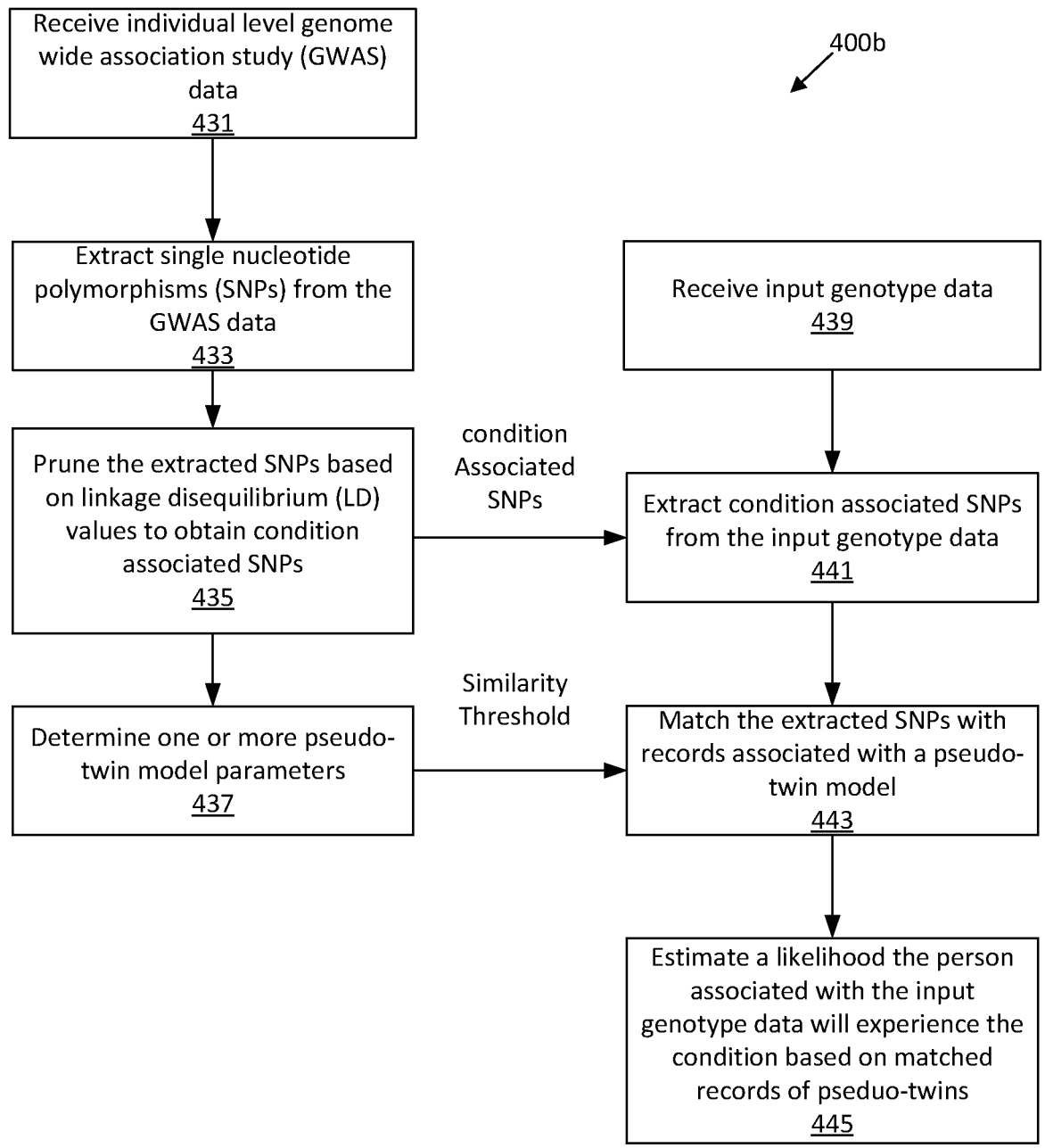

FIG. 4D shows an illustrative process 400b for estimating a likelihood that a given person will experience a medical condition by configuring and applying a pseudo-twin model. At acts 431, 433, 435, and 437, the pseudo-twin model may be configured as was described with reference to FIG. 4B. At acts 439, 441, 443, and 445, the pseudo-twin model may be applied to input genotype data as was described with reference to FIG. 4C.

Figure 5:
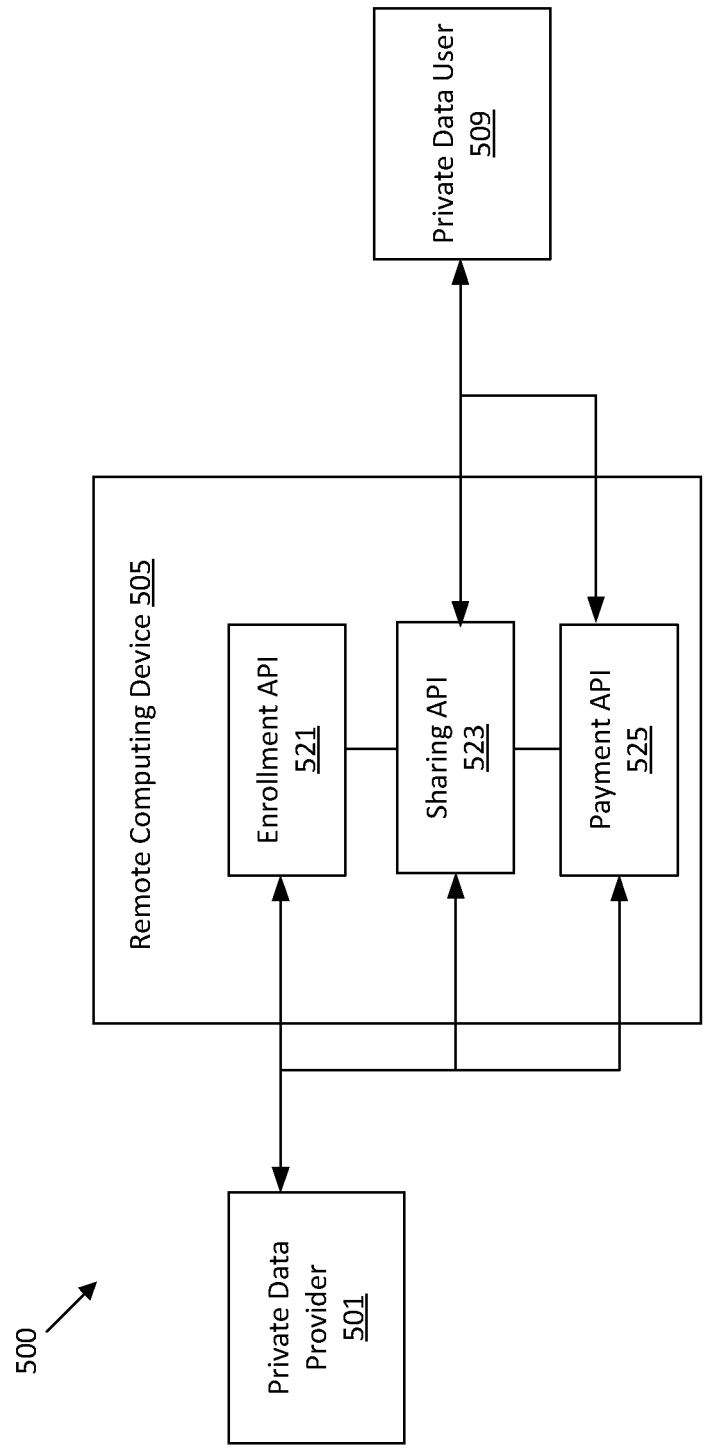
FIG. 5 shows an illustrative block diagram of computing devices for managing user access to private data.

FIG. 5 shows an illustrative block diagram of a system 500 for managing user access to private data. FIG. 5 illustrates a private data provider 501, a private data user 509, and a remote computing device 505 that is configured to host an enrollment API 521, a sharing API 523, and a payment API 525. The private data user may be an individual with private data for sharing, for example as was described with reference to private data providers 101a-101c in FIG. 1. The private data user 509 may be an application provider and/or application client as were described with reference to FIG. 1.

The remote computing device 505 may be any suitable computing device for hosting the APIs 521, 523, and 525, for example as was described with reference to API service 105 in FIG. 1. The remote computing device 505 may be one or more servers and/or nodes in a distributed ledger protocol.

The enrollment API 521 may be configured for allowing private data provider 501 to register to share private data, for example as was described with reference to FIG. 1. The private data provider may register to share private data using the enrollment API. The private data provider 501 may receive sharing credentials in response to registering. For example, credentials may include, but are not limited to, a user identification and cryptographic information. The user identification may be a unique identification provided to the private data provider 501. In some embodiments, the private data provider 501 may provide an uniquely identifying credential to the enrollment API in order to register. In some embodiments, a user identification may be a cryptographic key or an identifier based on a cryptographic key, for example private data provider 501 may be identified by an address used in a distributed ledger protocol such as a Bitcoin or Ethereum wallet address. In some embodiments, the private data provider 501 may register to share private data and receive cryptographic information, such as public and private cryptographic keys, that may be used to access secure systems for data sharing. In some embodiments, the private data provider 501 may receive a public cryptographic key that corresponds to a private cryptographic key held in a TEE.

The sharing API 523 may be configured to allow the sharing of private data. The private data user 509 may establish sharing conditions using the sharing API 523, and the private data provider 501 may agree to the sharing conditions and responsively share data. In some embodiments, the enrollment API 521 and the sharing API 523 may be implemented as a single API. For example, the private data user may enroll and share for each application. In some embodiments, the sharing API 523 may be implemented as a smart contract, which may be published to a distributed ledger by the private data user 509. The private data provider 501 and private data user 509 may agree to sharing conditions, for example, as was described with reference to FIG. 1. In some embodiments, the sharing API 523 may provide information identifying a TEE to one or both of the private data user 509 and the private data provider 501.

The payment API 525 may be configured to allow private data providers to be remunerated for contributing private data. In some embodiments, the sharing API 523 may trigger one or more functions of the payment API 525. For example, a private data user 509 that accesses sharing information through the sharing API 523 may also be required to provide payment via the payment API 525. The payment API 525 may also distribute remuneration to the private data provider 501 based on the sharing conditions established by the sharing API 523.

The inventors have recognized and appreciated that implementing fiat currency transfers for the payment API may present multiple counterparty risks and technical challenges, such as securing payment details and processing payments reliably. The payment API may therefore improve upon conventional, fiat payment processing by being implemented using a distributed ledger that is configured to make cryptocurrency payments. In some embodiments, smart contracts may trigger the transfer of cryptocurrency funds, for example upon an application being accessed using the same smart contract. In some embodiments, the payment API 525 may issue tokens to private data providers 501 according to the sharing conditions. In such embodiments, the payment API 525 may distribute payment to private date providers (e.g., 501) based on the distribution of tokens. For example, the payment API 525 may issue a total number of tokens to the private data providers that contribute to an application, and a private data user may 'rent' all or a portion of the tokens from the providers. Renting tokens may represent dividing a payment issued by the private data user to the holders of the tokens (e.g., the private data providers). In some embodiments, a subset of the total tokens may be selected for each use of the application, and the chance of a private data provider being selected is proportional to the portion of the total number of tokens the private data provider owns. For example, a private data user may pay $1 (e.g., in Ethereum digital currency) in order to rent 100 tokens to receive a prediction. A smart contract may then receive payment, grant the private data user access to the model, and then return each token to its owner along with $0.01 in payment per token.

The inventors have appreciated that an advantage of using cryptocurrency tokens is to evaluate the respective contributions of private data providers to the predictive model and encourage high quality data and honesty. A distributed ledger may be used to assign each private data provider a token, the value of which may be determined at a future point in time, such as when a predictive model is built. Thus, private data providers will get higher reward if their contributed data (e.g., their genotype data) is classified to be consistent with the self-reported label (e.g., the phenotype data) by the predictive model built from the larger population, and the assumption is that the majority of the population data is accurate. In this way, private data providers whose upload data such as DNA data similar to the majority of people reporting the same label may be rewarded and people may be encouraged to honestly report the data labels such as disease status. In some embodiments, the expected remuneration for a private data provider may be equal to the predicted probability that a self-reported label (e.g., an alleged medical condition status) is accurate. In some embodiments, the expected remuneration may be proportional to the probability that the private data provider is classified positively as having a medical condition. In some embodiments, the tokens may be distributed to each private data provider, after the model is configured, by multiplying the total number of tokens by the result of dividing a statistical measure of the value of the private data provider's contribution by a total value of the contributions of the private data providers.

Figure 6:
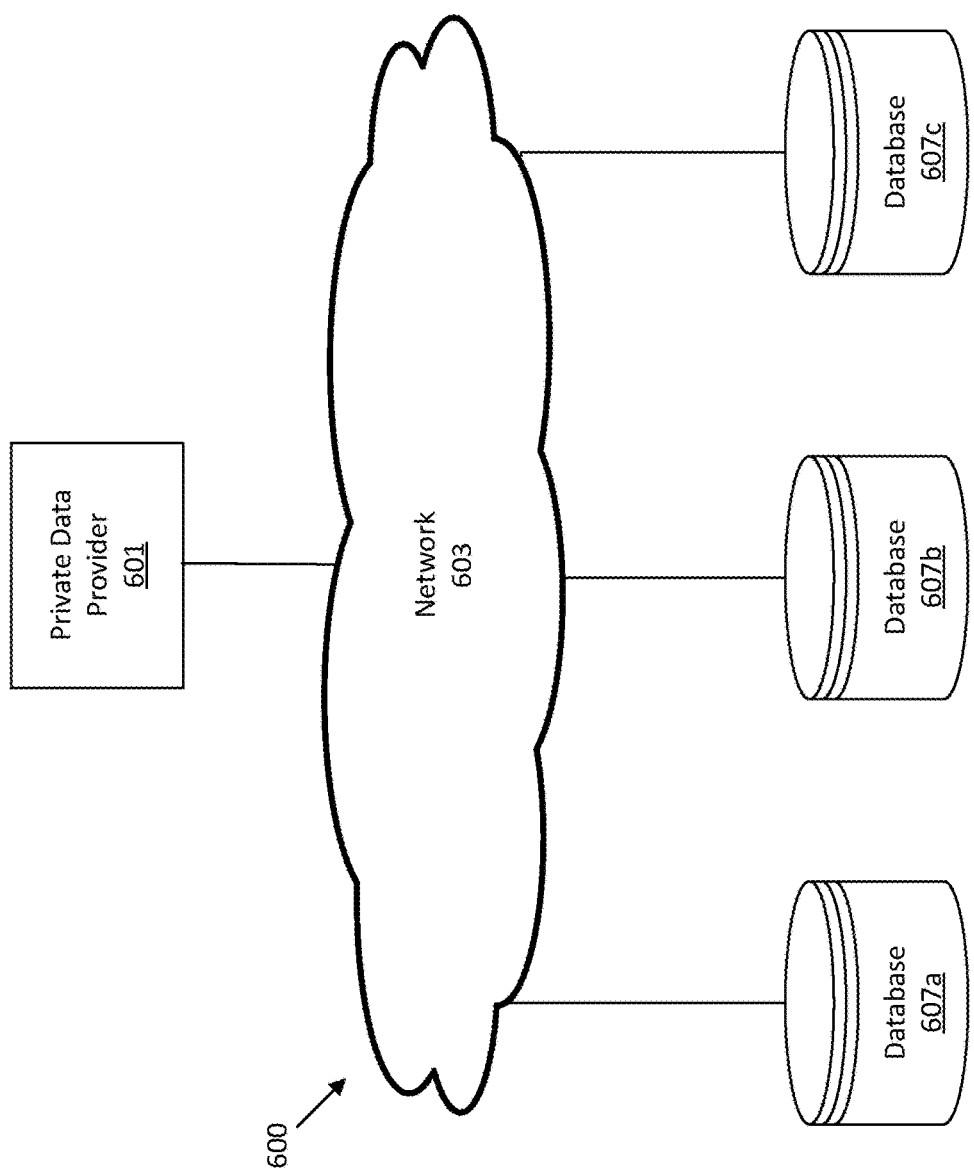
FIG. 6 shows an illustrative block diagram of a private data repository.

FIG. 6 shows an illustrative block diagram of a private data repository 600. FIG. 6 illustrates private data provider 601, network 603, and databases 607a-607c. (While FIG. 6 illustrates the private data repository 600 implemented in the form of one or more databases, it should be appreciated that embodiments are not limited to storing data in the form of a database or in any number of databases, and that other forms of storage may be used.) In some embodiments, private data providers (e.g., 101 and/or 701) may store encrypted private data in distributed data storage. For example, the private data may be encrypted using a cryptographic key associated with a TEE. The private data provider 601 may distribute shards of encrypted private data over the network 603 (e.g., according to a distributed hash table) to any suitable databases 607a-607c, which may be storage connected to or included in one or more TEEs.

In some embodiments, the private data repository 600 is used to store data related to one or more TEEs. For example, source code run in one or more TEEs, binaries that can be executed by a TEE, parameters of an application executed by a TEE, and/or any other suitable information.

Figure 7:
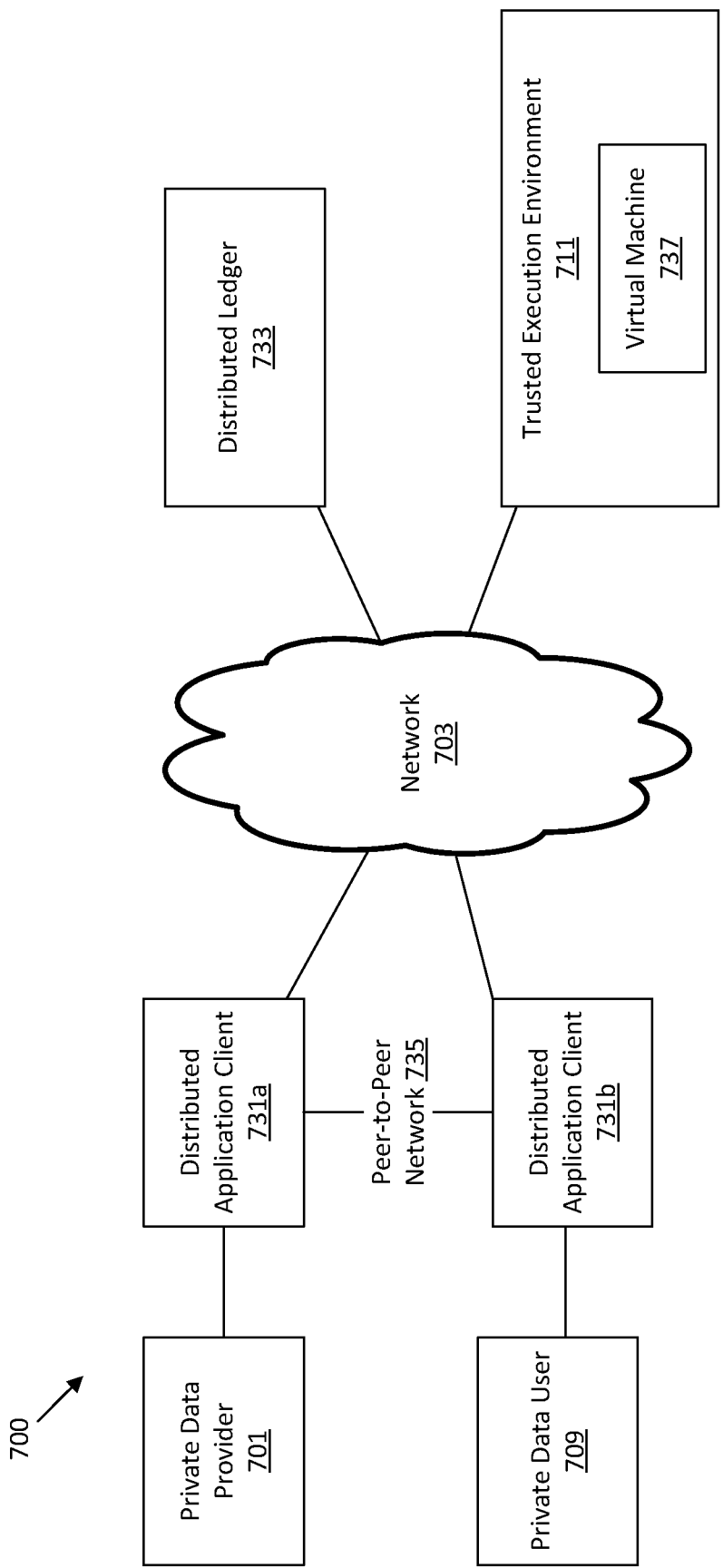
FIG. 7 shows an illustrative block diagram of a system for sharing private data.

FIG. 7 shows an illustrative block diagram of a system 700 for sharing private data. FIG. 7 illustrates a private data provider 701, private data user 709, distributed application clients 731a and 731b, peer-to-peer network 735, network 703, distributed ledger 733, TEE 711, and virtual machine 737. The system 700 may be operable to allow private data providers (e.g., 701) to share private data with private data users 709. The distributed ledger 733, as described with reference to FIGS. 1, 5, and 8, may store entries, including smart contracts, related to private data sharing.

Private data provider 701 may have private data to share, as was described with reference to private data providers 101a-101c in FIG. 1. Private data user 709 may make use of the shared private data, for example to train a model or purchase access to a model. Private data user 709 may operate as was described with reference to application provider 109 and application client 113 in FIG. 1.

Each of the private data provider 701 and the private data user 709 may utilize a respective distributed application client 731a&731b. Each distributed client application 731a-731b may be configured to interact with the distributed ledger 733, for example by publishing distributed ledger entries in accordance with one or more smart contracts. Each distributed application client 731 and 731b may be connected to the peer-to-peer network 735, which may be used for communicating with other distributed application clients. Any suitable peer-to-peer messaging system or protocol may be used. The peer-to-peer communication may be performed pseudonymously to prevent information about the private data providers from leaking to peer-to-peer messaging participants. TEE 711, one or more public repositories, and/or any other suitable computing devices may be connected to and communicate on the peer-to-peer network 735. In some embodiments, peer-to-peer identifiers of computing devices (e.g., TEE 711 and/or virtual machine 737) are stored in a distributed ledger. In some embodiments, the distributed application client 731a may be configured to perform the method described with reference to FIGS. 11A&B. Distributed application clients are also described with reference to FIG. 9.

In some embodiments, the distributed application client 731a may be configured to enable the private data provider to register to share private data, share private data according to one or more sharing conditions, be remunerated for sharing private data, and/or read and write any other relevant information to and from the distributed ledger. Similarly, distributed application client 731b may allow the private data user 709 to publish sharing conditions to the distributed ledger 733, purchase access to one or more applications in the TEE 711 and/or virtual machine 737, and/or read and write any other relevant information to and from the distributed ledger.

The TEE 711 may operate as is described with reference to execution environment 111, TEE 211, and/or TEE 1011. In the example of FIG. 7, the TEE 711 hosts the virtual machine 737. In some embodiments, the virtual machine may include a protected memory space for data and instructions. In some embodiments, the virtual machine may run using audited or trusted code. In some embodiments, the virtual machine is configured to interpret a limited set of instructions that operate on private data. In such embodiments, data privacy and security may be enforced by checking that an application submitted to and/or running in the virtual machine 737 adheres to the limited instruction set without a more complex auditing process. In some embodiments, the TEE 711 may host multiple virtual machines 737. Each virtual machine 737 may be owned and/or controlled by a particular private data user or provider. Information attesting to the identity and/or security of the virtual machine may be stored in the distributed ledger 733.

Figure 8:
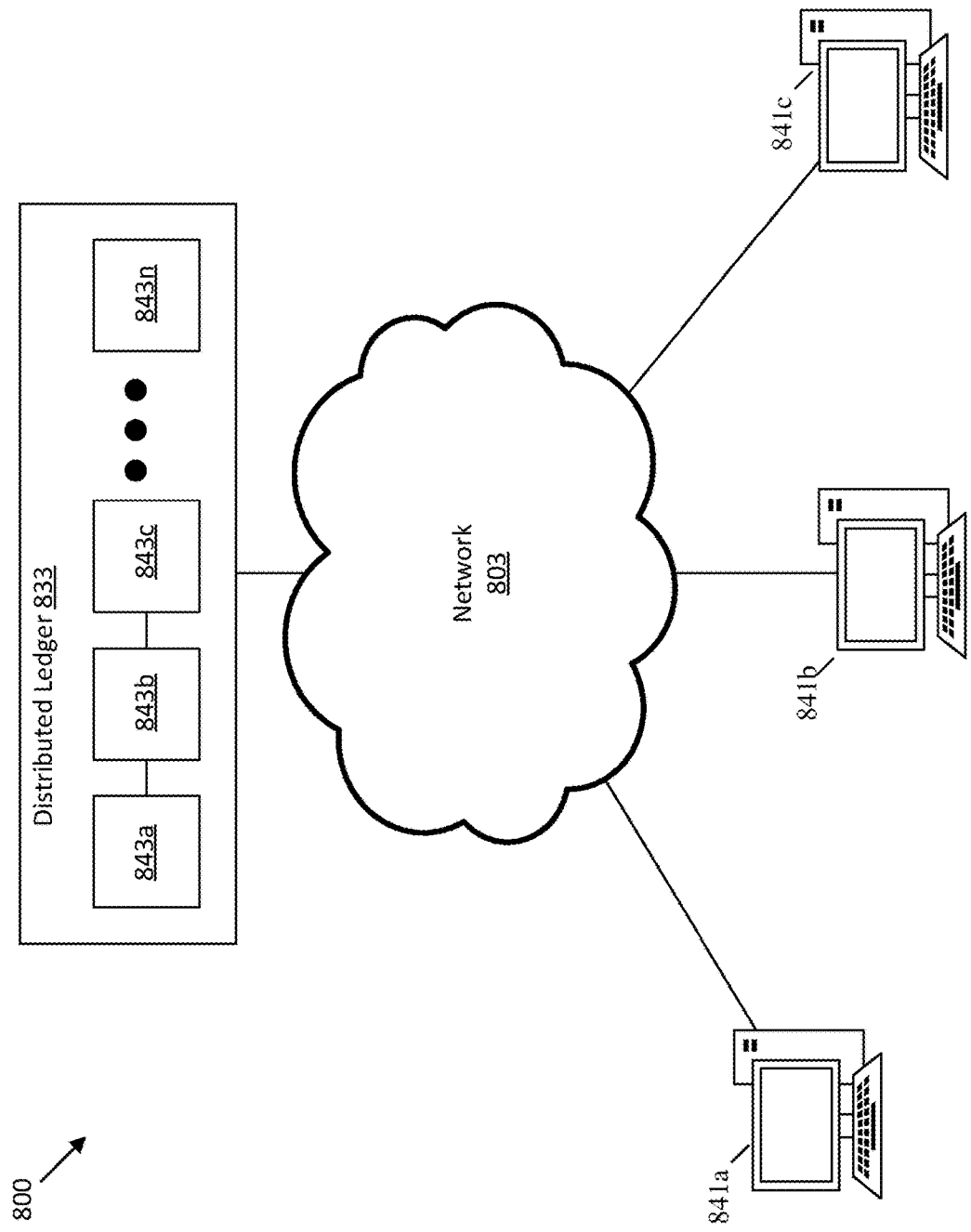
FIG. 8 shows an illustrative embodiment of a distributed ledger.

FIG. 8 shows an illustrative embodiment of a distributed ledger 833. FIG. 8 illustrates a system 800 for maintaining a distributed ledger 833. In particular, FIG. 8 shows distributed ledger nodes 841a, 841b, and 841c, connected by a network 803 (e.g., the internet), and the distributed ledger 833, which includes distributed ledger entries 843a, 843b, 843c, . . . , and 843n.

The distributed ledger is shared among multiple distributed ledger nodes 841a-841c and is used to record and check transactions in a cryptographically secure manner. In some embodiments, while new transactions may be appended to the distributed ledger, past transactions cannot be altered without breaking a chain of cryptographic proofs. For example, each distributed ledger entry 841a-843n may include a hash value computed using one or more previous entries as input. Distributed ledgers may therefore be used to publicly record cryptocurrency transactions from one individual to another. In some embodiments, computing devices besides the nodes 841a-841c may access and interact with the distributed ledger 833. In some embodiments, requested transactions on the distributed ledger 833 are transmitted to the nodes 841a-841c, which engage in a protocol for adding an entry to the distributed ledger, which may be referred to as mining. In some embodiments, distributed ledger entries may identify transfers of an amount of a cryptocurrency from one wallet address (e.g., a unique identifier an individual uses to possess and control cryptocurrency) to another wallet address, which may be used to remunerate private data providers. The inventors have also recognized and appreciated that the distributed ledger 833 may be used in applications other than digital currency. For instance, the distributed ledger 833 may be used to implement a trust structure to allow attestations (e.g., that prove the security of a TEE) to be visible to and relied upon across multiple entities. The distributed ledger 833 may also store smart contracts, which may implement an API. In some embodiments, the configuration of a smart contract may be used to provide instructions that are executed by the node of nodes 841a-841c that adds an entry interacting with the smart contract to the distributed ledger 833. For example, a smart contract may include pre-defined contract terms established/ agreed to by all counterparties, the terms including, as non-limiting examples, token/digital currency addresses, algorithm instructions, a format or data to be shared, relevant storage addresses, user identifications, costs for computation related to the contract, and/or conditions such as data validation conditions, application evaluation/use conditions, and/or temporal conditions. As a further example, a smart contract may include events that may trigger the execution of all or portions of the instructions in the smart contract such as a data transfers, an amount of data sharing, and/or computations associated with an application associated with the smart contract. The terms of a smart contract may govern the execution of the smart contract, including value transfers and other operations in the distributed ledger, and/or the settlement of the smart contract.

As an illustrative example, distributed ledger entry 843a may store a smart contract that allows a private data provider to register to share private data according to sharing conditions and grants access to an application in a TEE in exchange for a digital currency fee. Distributed ledger entry 843b may include an attestation for a TEE. Distributed ledger entry 843c may include an indication that a private data provider agreed to the sharing conditions in distributed ledger entry 843a and/or that the private data was shared with the TEE attested for in distributed ledger entry 843b. Distributed ledger entry 843n may store a record of a transaction providing remuneration to the private data provider in exchange for access to an application in the TEE.

It should be appreciated that the distributed ledger 833 may be implemented in any suitable manner. For instance, in some embodiments, one or more directed acyclic graphs (e.g. IOTA 15 Tangle), hashgraphs (e.g. Swirlds), hash trees (e.g. Guardtime keyless signatures infrastructure), and/or distributed ledgers with no globally-shared chain (e.g. R3 Corda), may be used in addition to, or instead of, one or more blockchains.

Figure 9:
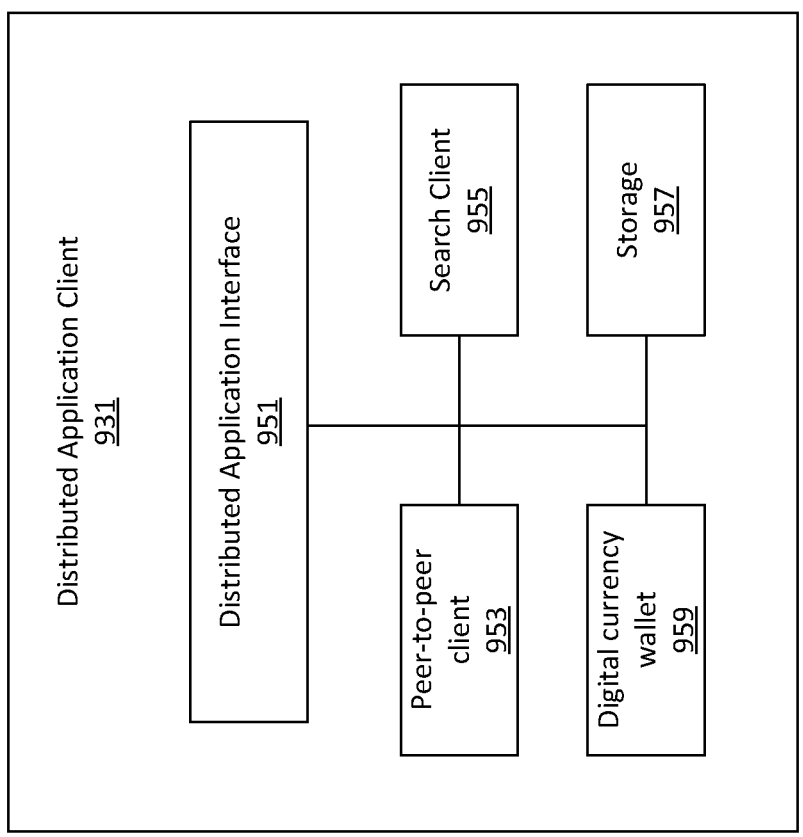
FIG. 9 shows an illustrative block diagram of a distributed application client.

FIG. 9 shows an illustrative block diagram of a distributed application client 931, which includes a distributed application interface 951, a peer-to-peer client 953, a search client 955, a storage 957, and a digital currency wallet 959. The distributed application client may be used to communicate with one or more distributed ledgers, for example as was described with reference the FIGS. 1 and 7. In some embodiments, APIs, such as the APIs described with reference to FIGS. 1 and 5, may be implemented using a smart contract stored in a distributed ledger and a distributed application client 931 configured to interact with the instructions stored in the smart contract. The distributed application interface 951 may include an suitable interface for receiving user input and interacting with one or more distributed ledgers based on the user input. It is not required that the distributed application client implement a full distributed ledger protocol and/or maintain or verify a copy of the distributed ledger. The storage 957 may store information related to the distributed ledger, private data, and/or any other suitable data.

The peer-to-peer client 953 may be used for communicating with other distributed application clients. Any suitable peer-to-peer messaging system or protocol may be used. The peer-to-peer communication may be performed pseudonymously to prevent information about the private data providers from leaking to peer-to-peer messaging participants. A suitable method of ensuring private peer-to-peer communication is described with reference to FIG. 12C.

In some embodiments, peer-to-peer client 953 is configured to generate a peer-to-peer identifier. For example, the peer-to-peer client 953 may use a seed phrase to generate a number of key pairs, each of which may be used as a messaging account. In some embodiments, the user of the peer-to-peer client 953 may change accounts at any suitable time.

In some embodiments, the distributed application client 93 may be configured to perform user authentication and/or access control. For example, a user may log into the distributed application client 931 by providing an account name and the private key of their account, which may be encrypted with a password. In some embodiments, the distributed application client 931 authenticates (e.g., grants access to data and/or control) the user if the provided private key can decrypt data associated with the account name. In some embodiments, the account name may be local to the distributed application client. In some embodiments, the peer-to-peer client 953 is used in conjunction with the search client 955 to allow users to search for private data. The search client 955 may receive (e.g., through the peer-to-peer client 953) requests for a desired characteristic of private data. In some embodiments, the search client may store (e.g., using storage 957) information that may be used to index a search into the private data. For example, one or more hash values may be computed using the private data and stored, the incoming search requests may then include a desired hash value. Searching private data is also described with reference to FIGS. 12A&B.

The digital currency wallet may be configured to interact with a distributed ledger to manage transaction in a digital currency. For example, the digital currency wallet 959 may be used to receive remuneration for sharing private data, provide payment for access to private data, and/or provide any other suitable digital currency transaction. The digital currency wallet 959 may also be used to store tokens that are used to distribute remuneration for sharing private data.

Figure 10:
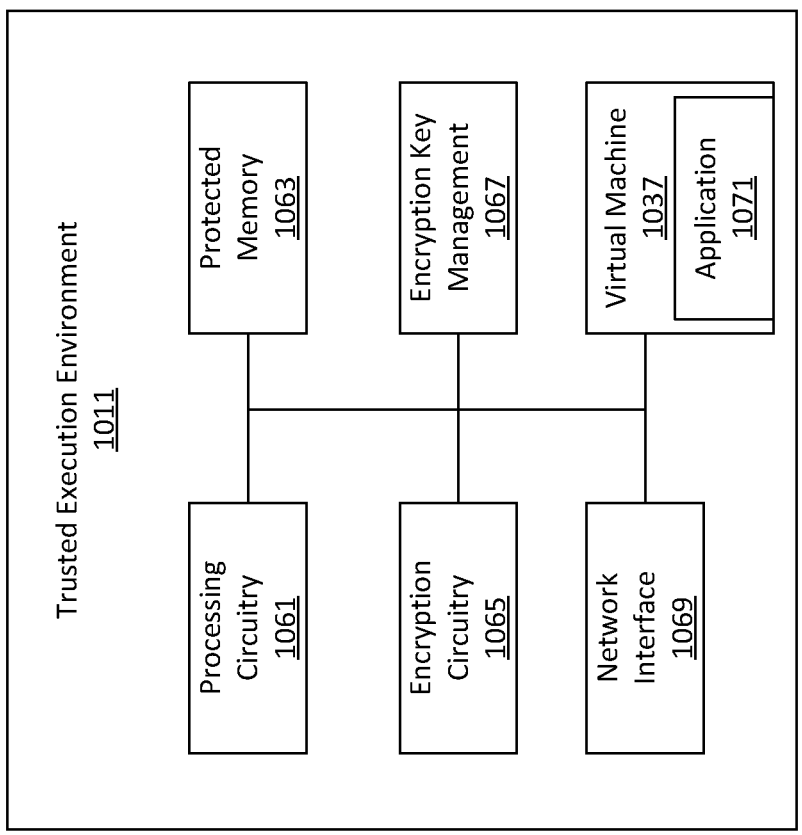
FIG. 10 shows an illustrative block diagram of a trusted execution environment.

FIG. 10 shows an illustrative block diagram of a trusted execution environment 1011. The TEE 1011 may operate as is described with reference to execution environment 111, TEE 211, and/or TEE 711. The TEE 1011 includes processing circuitry 1061, protected memory 1063, encryption circuitry 1065, encryption key management 1067, network interface 1069, and virtual machine 1037 which hosts application 1071.

The processing circuitry may be any suitable processing circuitry including a processor, a system on a chip (SoC), a field programmable gate array (FPGA), an application specific integrated circuit (ASIC), and/or any other suitable processor. The processing circuitry 1061 may be configured to access the protected memory 1063, which may be secure and trusted. The encryption circuitry 1065 may perform any necessary cryptographic functions, including hashing and/or encryption of inputs, using one or more cryptographic keys. In some embodiments, the encryption key management 1067, maintains one or more encryption keys, such as private and public key pairs. Key pairs may be generated and maintained for each application, virtual machine, private data provider, private data user, or in any suitable manner. The network interface may be any suitable interface for network communication (e.g., over a wired or wireless connection to the internet). In some embodiments, the network interface 1069 may be configured to interact with one or more distributed ledgers to publish and retrieve information and/or entries to and from the distributed ledger(s).

In some embodiments, the all or a portion of the elements of the TEE 1011 may be implemented using Intel Corporation® Software Guard Extensions (Intel® SGX) or ARM® TrustZone. In some embodiments, the TEE 1011 may be virtualized to present one or more TEEs as a single, virtual TEE to users. For example, users may receive a single encryption key for interacting with the TEE, and the private data shared using the one key may be decrypted and shared within the TEE (e.g., by the encryption circuitry 1065 and encryption key management 1067).

The virtual machine 1037 may operate as was described with reference to virtual machine 737 in FIG. 7. The virtual machine 1037 may run on one or more virtual machines either concurrently or through migration of the virtual machine 1037. In some embodiments, each virtual machine is assigned to at most one application 1071 to isolate workloads and ensure security. In some embodiments, the virtual machine 1037 may be owned and controlled by an individual such as an application provider. In some embodiments, the TEE 1011 may be utilized to host one or more applications 1071 for facilitating techniques described herein. For example, a TEE 1011 may be configured to host an application 1071 for indexing private data for searching.

FIGS. 11A-D show illustrative process flows for sharing private data. The illustrated process 1100 may be executed using a distributed application (e.g., distributed applications 731*a*, 731*b*, and/or 931). The process 1100 begins at act 1101, where private data is registered for sharing. The private data may be registered for sharing using an API and/or a smart contract in a distributed ledger, for example as were described with reference to FIGS. 1, 5, and 7.

At act 1103, security information to the secure private data may be obtained from a secure execution environment, which may be referred to as a trusted execution environment. In some embodiments, a trusted execution environment may provide one or more encryption keys to the private data provider that is registered to share private data. The encryption key(s) may then be used to secure the private data via encryption.

At act 1105, one or more attestation reports identifying the secure execution environment may be stored and/or accessed in a distributed ledger. Storing the attestation report in a distributed ledger may ensure that the report is publicly available and yet still immutable and, therefore, trustworthy. The attestation report may be used to ensure that the secure execution environment and/or the private data remain secure and may be trusted. Furthermore, an attestation report may also allow a user to determine that a network address that purportedly belongs to a TEE is attested to belong to a TEE. In some embodiments, an attestation report may be accessed, in the distributed ledger, that indicates that the TEE is secure. In some embodiments, an attestation report may be stored in the distributed ledger to indicate that the TEE and/or the private data are secure.

At act 1107, an indication that the private data has been registered for sharing is stored in a distributed ledger. At act 1109, the secured private data is transmitted to the secure execution environment in response to an instruction granting access. In some embodiments, the private data provider may publish a distributed ledger transaction using a smart contract to agree to sharing the private data and receive an indication that the transaction has posted to the distributed ledger. In response, the private data provider may transmit the private data to a TEE. In some embodiments, the private data may be in a TEE, and access may be granted based on an instruction to grant access.

FIG. 11B shows an illustrative process flow 1110 for sharing private data. The illustrated process 1110 may be executed using a distributed application (e.g., distributed applications 731a, 731b, and/or 931). The process 1110 begins at act 1111, where a request to share private data according to sharing conditions is transmitted. The request may be transmitted to a distributed ledger. The request may be based on a smart contract, which may publish the sharing conditions, in a distributed ledger, for example as were described with reference to FIGS. 1, 5, and 7.

At act 1113, the security of a TEE identified in the sharing conditions may be verified based on an attestation in the distributed ledger. As was described with reference to act 1103, of FIG. 11A, storing the attestation report in a distributed ledger may ensure that the report is publicly available and yet still immutable and, therefore, trustworthy. The attestation report may be used to ensure that the secure execution environment remains secure and may be trusted. Furthermore, the attestation report may also allow a user to determine that a network address that purportedly belongs to a TEE is attested to belong to a TEE.

In some embodiments, the attestation report and/or the sharing conditions may include a public key encryption key that corresponds to a private encryption key held by the TEE. In some embodiments, the public key is obtained by the private data provider in any suitable manner. At act 1115, the public encryption key may be is used to encrypt the private data. At act 1117, the encrypted private data is transmitted to the TEE identified in the sharing conditions. In response, a confirmation that the private data was used in the generation, training, and/or configuration of a model and/or application may be received and/or published to the distributed ledger. An ownership interest (e.g., tokens indicating a private data user contributed private data) may also be published to one or more distributed ledgers. At act 1119, remuneration (e.g., a digital currency transfer) is received according to the sharing conditions, for example in response to a private data user purchasing access to the private data.

FIG. 11C shows an illustrative process flow 1120 for providing an application to receive private data. The illustrated process 1120 may be executed using a distributed application (e.g., distributed applications 731a, 731b, and/or 931). The process 1120 begins at act 1121, where executable instructions are transmitted to a secure execution environment. In some embodiments, the executable instructions may include a series of instructions for execution by a virtual machine hosted by the secure execution environment. The instructions may, when executed, cause the virtual machine to configure and/or execute an application. For example, the instructions may include instructions to configure and to apply a pseudo-twin model and/or a model for detecting inauthentic genotype data.

At act 1123, a ledger entry is transmitted to a distributed ledger identifying the secure execution environment and one or more parameters associated with the executable instructions. In some embodiments, the ledger entry may include a smart contract and may specify one or more sharing conditions. In some embodiments, the one or more parameters may include identification information for the execution environment, sharing conditions, information about the model and the private data needed, and/or any other suitable parameters.

FIG. 11D shows an illustrative process flow 1130 for operating on shared private data. The illustrated process 1130 may be executed using a TEE (e.g., execution environment 111, TEE 711, and/or TEE 1011). The process 1130 begins at act 1131, where a request for a prediction from model and encrypted private input data are received. The model may be any suitable model, such as a pseudo-twin model and/or a model for detecting inauthentic genotype data. At act 1133, the private input data is decrypted, for example using a private key held in the TEE.

At act 1135, a prediction is performed using the model. The prediction may be performed by executing, or causing to be executed, a series of instructions that correspond to the model. In some embodiments, the model may be implemented in a respective virtual machine. At step 1137, the result of applying the prediction model to the private input data are output. In some embodiments, the output of the model is transmitted to the source of the request received at act 1131. It should be appreciated that the process 1130 is not limited to models, and any suitable workload or application may be computed using suitable input data without departing from the scope of the present disclosure.

Figure 12A:
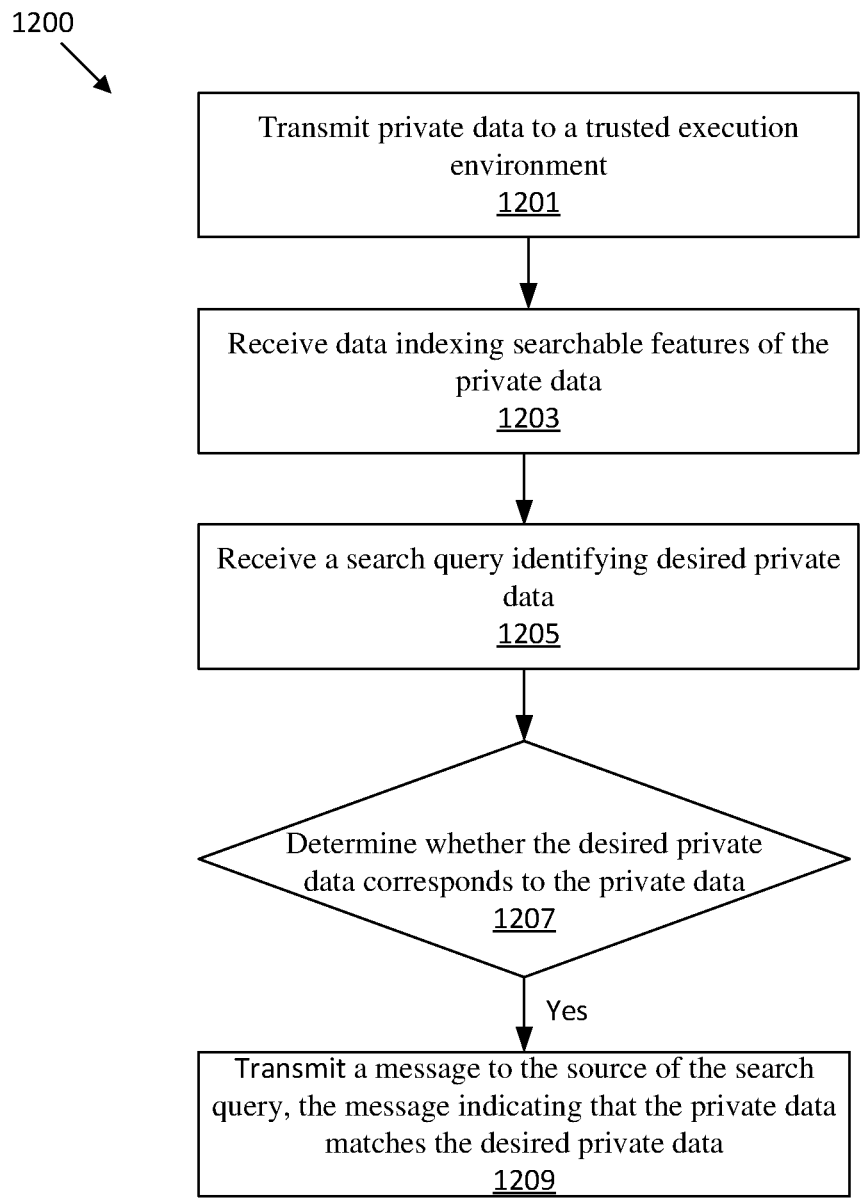

FIGS. 12A-C show illustrative process flows for search and communication regarding private data. FIG. 12A shows an illustrative process 1200 for enabling searching for private data. The illustrated process 1200 may be executed using a distributed application (e.g., distributed applications 731a, 731b, and/or 931). The process 1200 begins at act 1201, where private data is transmitted to a TEE. In response, at act 1203, data indexing searchable features of the private data is received from the TEE. In some embodiments, the TEE may compute a hash or other suitable indexes using all or portions of the private data. For example, the data indexing searchable features may include multiple hashes computed over multiple respective sets of SNPs in genotype data.

At act 1205, a search query is received (e.g., over a peer-to-peer messaging system) identifying desired private data. In some embodiments, the desired private data may be identified by a search index value that corresponds to the desired private data. For example, a researcher searching for a particular genotype may compute a hash of the desired genotype and/or select a precomputed hash from selectable search options. At act 1207, it is determined whether the desired private data corresponds to the private data. For example, a hash value received from the TEE may be compared to a hash received in the search query. If the private data does not match the desired private data, in some embodiments, a message may be transmitted to the source of the search query indicating the lack of a match. In some embodiments, no action is taken when the desired private data does not match. At act 1209, when the private data matches the desired private data, a message is transmitted to the source of the search query indicating that the private data matches the desired private data.

In some embodiments, the search described with reference to FIG. 12A may be broadcast over a peer-to-peer network, with the matching being performed by each recipient. The inventors have appreciated, therefore, that it may be beneficial to validate reported matches. At act 1211, an individual reporting a search match may receive a request to validate a characteristic of the private data (e.g., the desired characteristic in a search). At act 1213, the private data may be transmitted to a TEE for validation. The TEE may be trusted by both parties to validate the private data characteristics in private (e.g., without revealing information to either party).

The inventors have also appreciated that it may be beneficial for communication, including searching, to be pseudonymous in order to protect individual privacy and security.

Thus, FIG. 12C shows an illustrative process 1220 for secure peer-to-peer communication. At act 1221, a message (e.g., a response to a search query) is generated. At act 1223, two parties participate in the computation of a garbled circuit to obscure the identity of at least one of the sender and receiver. In some embodiments, each distributed application client creates a new peer-to-peer messaging account and/or identifier for responding to each search query. In some embodiments, the garbled circuit is evaluated by the distributed application client of a private data provider and a remote computing device. For example, the distributed application client may input all or a portion of the message and/or an identifier of the recipient into a garbled circuit generated by a server. Since garbled circuits provide security, the remote computing device is not required to be a TEE and does not require any specialized hardware components.

A garbled circuit refers to techniques for secure multi-party computation. It should be apparent to a person of ordinary skill in the art that a garbled circuit may be implemented according to the garbled circuit protocol credited to Andrew Yao. In some implementations, two parties or more may evaluate a garbled circuit without any party being able to discern any information about the inputs of any other party. For simplicity, the garbled circuits described herein will involve two parties (e.g., the distributed application client 731a and a remote computing device) but it should be appreciated that multiparty garbled circuits may be implemented.

In some embodiments, a garbled circuit includes one or more logic gates, which are based on corresponding truth tables, one party acting as a constructor (e.g., the remote computing device), and one party acting as an evaluator (e.g., the distributed application client). The constructor constructs the garbled circuit. For each logic gate in the garbled circuit, the constructor generates a set of parameters. The parameters include input keys that correspond to each possible input for the parties. For example, the constructor may generate four input keys, one for each party to input a zero or one into the gate. The input keys may be randomly generated numbers. The constructor may also assign an output key to each possible output of the logic gate. For example, two labels may be assigned where the possible outputs are zero and one. In some embodiments, each output of a four entry truth table may have a unique output label, but this may require substantially more resources to implement. Pairs of the input keys are then used to encrypt each output that corresponds to inputting the pair of input keys to the gate. For example, the key for party A to input '1' and the key for party B to input '0' would be used to encrypt the output that corresponds to party A inputting '1' and party B inputting '0.' After the constructor assigns the keys to the inputs and outputs, the rows of the truth table for the logic gate are randomly permuted (or 'garbled') such that the true output value cannot be determined from the row.

The constructor then provides the encrypted outputs for each of the gates in the garbled circuit to the evaluator. In order to decrypt the outputs and evaluate the garbled circuit, the evaluator will need to receive the input keys from the constructor. The constructor may send the keys corresponding to the constructor's input to the evaluator. The evaluator is ignorant of the mapping between keys and true inputs and, thus, receives no information about the constructor's input. In order to completely evaluate the garbled circuit, the evaluator must receive the proper keys for the evaluator inputs. This creates the potential for the constructor to learn the evaluator's input, which can compromise the authentication process.

In some embodiments, the evaluator input keys are transferred according to an oblivious transfer protocol. Oblivious transfers allow a first party to receive one piece of information out of many possible options held by a second party. The transfers are oblivious because the second party does not learn the first party's chosen input and the first party does not learn the other possible options not transferred. For example, the evaluator may receive the input key corresponding to zero without learning what random number was assigned as an input key for one. If the evaluator received both valid input keys, it may be possible to determine the inputs from the constructor.

It should be appreciated that various implementations of the garbled circuit protocol may have respective benefits and costs, for example with respect circuit complexity or hardware design. It should be appreciated that modifications may be made to the garbled circuit protocol without departing from the scope of the disclosure.

In some embodiments, a TEE may be configured to securely map pseudonymous peer-to-peer messaging identifiers to a corresponding network address, or other suitable identifiers. In such embodiments, the pseudonymous peer-to-peer messaging identifiers may obscure the true identity of message senders and/or recipients. The corresponding network address may be used to directly identify a sender and/or recipient and address a message.

Figure 13:
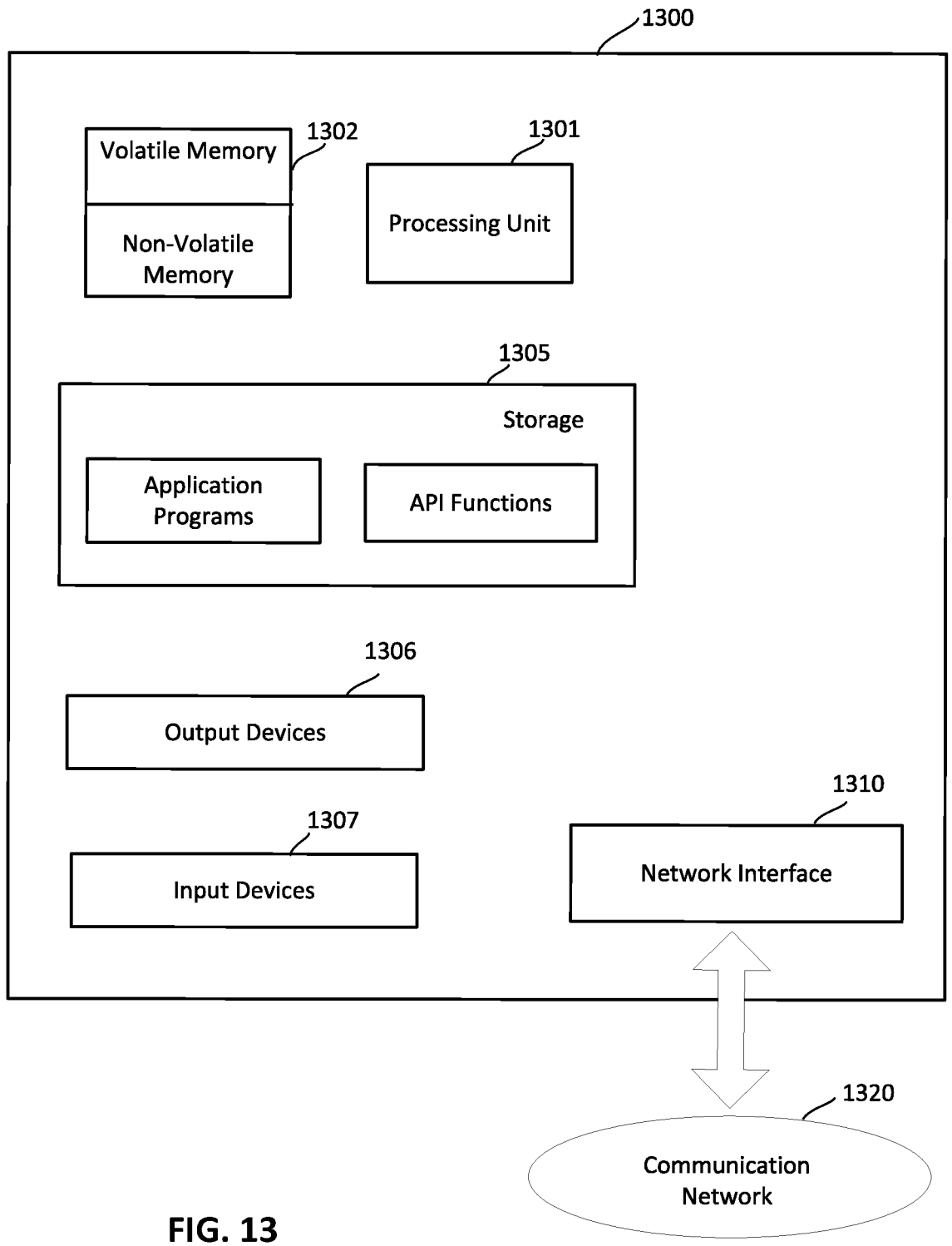
FIG. 13 shows an illustrative computing system on which any aspect of the present disclosure may be implemented.

FIG. 13 shows, schematically, an illustrative computer 1300 on which any aspect of the present disclosure may be implemented. In the embodiment shown in FIG. 13, the computer 1300 includes a processing unit 1301 having one or more processors and a non-transitory computer-readable storage medium 1302 that may include, for example, volatile and/or non-volatile memory. The memory 1302 may store one or more instructions to program the processing unit 1301 to perform any of the functions described herein. The computer 1300 may also include other types of non-transitory computer-readable medium, such as storage 1305 (e.g., one or more disk drives) in addition to the system memory 1302. The storage 1305 may also store one or more application programs and/or external components used by application programs (e.g., software libraries), which may be loaded into the memory 1302.

The computer 1300 may have one or more input devices and/or output devices, such as devices 1306 and 1307 illustrated in FIG. 13. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards and pointing devices, such as mice, touch pads, and digitizing tablets. As another example, the input devices 1307 may include a microphone for capturing audio signals, and the output devices 1306 may include a display screen for visually rendering, and/or a speaker for audibly rendering, recognized text.

As shown in FIG. 13, the computer 1300 may also comprise one or more network interfaces (e.g., the network interface 1310) to enable communication via various networks (e.g., the network 1320). Examples of networks include a local area network or a wide area network, such as an enterprise network or the Internet. Such networks may be based on any suitable technology and may operate according to any suitable protocol and may include wireless networks, wired networks or fiber optic networks.

Having thus described several aspects of at least one embodiment, it is to be appreciated that various alterations, modifications, and improvements will readily occur to those skilled in the art. Such alterations, modifications, and improvements are intended to be within the spirit and scope of the present disclosure. Accordingly, the foregoing description and drawings are by way of example only.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the concepts disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the present disclosure described above. The computer-readable medium or media can be transportable, such that the program or programs stored thereon can be loaded onto one or more different computers or other processors to implement various aspects of the present disclosure as described above.

The terms "program" or "software" are used herein to refer to any type of computer code or set of computer-executable instructions that can be employed to program a computer or other processor to implement various aspects of the present disclosure as described above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various features and aspects of the present disclosure may be used alone, in any combination of two or more, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the concepts disclosed herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

What is claimed is:

1. A computer-implemented method for sharing private data, the method comprising:
   registering private data for sharing within a secure platform for exchange of private information, wherein registering the private data comprises:
      obtaining, from a secure execution environment, security information to secure private data;
      storing, in a first distributed ledger, an attestation report identifying that the secure execution environment has been secured; and
      storing, in a second distributed ledger, an identification that the private data has been registered for sharing within the secure platform; and
   in response to receiving an instruction from a user granting access to the secured private data, triggering transmission of the secured private data to the secure execution environment to be processed, wherein the triggering comprises recording, in the second distributed ledger, an indication that the access has been granted to the secured private data.

2. The method of claim 1, wherein the method further comprises securing the private data within an enclave associated with at least one Trusted Execution Environment (TEE).

3. The method of claim 2, wherein obtaining, from a secure execution environment, security information to secure private data comprises obtaining a public encryption key that corresponds to a private encryption key in the secure execution environment.

4. The method of claim 1, wherein the method further comprises securing the private data via a virtual machine executing within the secure execution environment.

5. The method of claim 1, wherein the method further comprises, in response to receiving the instruction from the user granting access to the secured private data:
receiving a confirmation that the secured private data was used in generation of a private information model and that an ownership interest by the user in the private information model has been recorded in the second distributed ledger.

6. The method of claim 1, wherein the method further comprises:
receiving a search query identifying desired private data;
determining whether the desired private data corresponds to the private data; and
in response to determining that the private data corresponds to the desired private data, transmitting a message to a source of the search query, the message indicating that the private data corresponds to the desired private data.

7. The method of claim 1, the method further comprising:
transmitting the secured private data to a second secure execution environment; and
receiving one or more search indices indicating one or more respective characteristics of the private data.

8. The method of claim 1, the method further comprising:
receiving a request to validate a characteristic of the private data; and
in response to the request, transmitting the secured private data to a second secure execution environment configured to validate the characteristic.

9. The method of claim 1, the method further comprising:
generating a message; and
transmitting the message, wherein transmitting the message comprises evaluating a garbled circuit, generated by a remote computing device, configured to obscure respective identities of a sender and a recipient of the message.

10. The method of claim 1, the method further comprising, in response to transmitting the secured private data to the secure execution environment, receiving an indication of a remuneration via the distributed ledger.

11. The method of claim 10, the method further comprising:
in response to transmitting the secured private data to the secure execution environment, receiving an indication that a task making use of the private data has completed; and
subsequent to receiving the indication that the task making use of the private data has completed, receiving an indication of an expected value of a future remuneration via the distributed ledger.

12. The method of claim 1, the method further comprising storing the secured private data in a repository.

13. The method of claim 1, wherein the private data comprises genomic data, social information data, picture data, phenotypic data, medical data, financial data, and/or insurance data.

14. At least one non-transitory computer-readable storage medium having encoded thereon executable instructions that, when executed by at least one processor, cause the at least one processor to carry out a method for sharing private data, the method comprising:
registering private data for sharing within a secure platform for exchange of private information, wherein registering the private data comprises:
obtaining, from a secure execution environment, security information to secure private data;
storing, in a first distributed ledger, an attestation report identifying that the secure execution environment has been secured; and
storing, in a second distributed ledger, an identification that the private data has been registered for sharing within the secure platform; and
in response to receiving an instruction from a user granting access to the secured private data, triggering transmission of the secured private data to the secure execution environment to be processed, wherein the triggering comprises recording, in the second distributed ledger, an indication that the access has been granted to the secured private data.

15. The at least one non-transitory computer-readable storage medium of claim 14, wherein the method further comprises, in response to receiving the instruction from the user granting access to the secured private data:
receiving a confirmation that the secured private data was used in generation of a private information model and that an ownership interest by the user in the private information model has been recorded in the second distributed ledger.

16. The at least one non-transitory computer-readable storage medium of claim 14, wherein the method further comprises:
receiving a search query identifying desired private data;
determining whether the desired private data corresponds to the private data; and
in response to determining that the private data corresponds to the desired private data, transmitting a message to a source of the search query, the message indicating that the private data corresponds to the desired private data.

17. The at least one non-transitory computer-readable storage medium of claim 14, wherein the method further comprises:
receiving a request to validate a characteristic of the private data; and
in response to the request, transmitting the secured private data to a second secure execution environment configured to validate the characteristic.

18. An apparatus comprising:
at least one processor; and
at least one storage medium having encoded thereon executable instructions that, when executed by the at least one processor, cause the at least one processor to carry out a method for sharing private data, the method comprising:
registering private data for sharing within a secure platform for exchange of private information, wherein registering the private data comprises:
obtaining, from a secure execution environment, security information to secure private data;
storing, in a first distributed ledger, an attestation report identifying that the secure execution environment has been secured; and
storing, in a second distributed ledger, an identification that the private data has been registered for sharing within the secure platform; and
in response to receiving an instruction from a user granting access to the secured private data, triggering transmission of the secured private data to the secure execution environment to be processed, wherein the triggering comprises recording in the second distributed ledger an indication that the access has been granted to the secured private data.

19. The apparatus of claim 18, wherein the method further comprises, in response to receiving the instruction from the user granting access to the secured private data:
- receiving a confirmation that the secured private data was used in generation of a private information model and that an ownership interest by the user in the private information model has been recorded in the second distributed ledger.

20. The apparatus of claim 18, wherein the method further comprises:
- receiving a search query identifying desired private data;
- determining whether the desired private data corresponds to the private data; and
- in response to determining that the private data corresponds to the desired private data, transmitting a message to a source of the search query, the message indicating that the private data corresponds to the desired private data.

21. The apparatus of claim 18, wherein the method further comprises:
- receiving a request to validate a characteristic of the private data; and
- in response to the request, transmitting the secured private data to a second secure execution environment configured to validate the characteristic.

* * * * *